(12) United States Patent
Tino et al.

(10) Patent No.: US 7,795,291 B2
(45) Date of Patent: Sep. 14, 2010

(54) SUBSTITUTED ACID DERIVATIVES USEFUL AS ANTI-ATHEROSCLEROTIC, ANTI-DYSLIPIDEMIC, ANTI-DIABETIC AND ANTI-OBESITY AGENTS AND METHOD

(75) Inventors: Joseph A. Tino, Lawrenceville, NJ (US); Peter T. W. Cheng, Princeton, NJ (US); Yan Shi, Flourtown, PA (US); Jun Li, Princeton, NJ (US); Ranjan Mukherjee, Churchville, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 495 days.

(21) Appl. No.: 11/773,545

(22) Filed: Jul. 5, 2007

(65) Prior Publication Data

US 2008/0009533 A1   Jan. 10, 2008

Related U.S. Application Data

(60) Provisional application No. 60/819,166, filed on Jul. 7, 2006.

(51) Int. Cl.
*A61K 31/421* (2006.01)
*C07D 263/30* (2006.01)
(52) U.S. Cl. .................. 514/374; 548/215; 548/235; 548/236
(58) Field of Classification Search .............. 548/215, 548/235, 236; 514/374
See application file for complete search history.

(56) References Cited

U.S. PATENT DOCUMENTS

| 6,414,002 | B1 | 7/2002 | Cheng et al. | |
|---|---|---|---|---|
| 6,653,314 | B2 * | 11/2003 | Cheng et al. | 514/256 |
| 6,727,271 | B2 * | 4/2004 | Cheng et al. | 514/374 |
| 6,919,358 | B2 * | 7/2005 | Cheng et al. | 514/340 |
| 7,053,106 | B2 * | 5/2006 | Cheng et al. | 514/333 |
| 7,084,162 | B2 * | 8/2006 | Cheng et al. | 514/374 |
| 7,241,780 | B2 * | 7/2007 | Cheng et al. | 514/340 |

OTHER PUBLICATIONS

U.S. Appl. No. 11/773,564, Cheng et al.

* cited by examiner

*Primary Examiner*—Golam M Shameem
(74) *Attorney, Agent, or Firm*—Burton Rodney

(57) ABSTRACT

Compounds are provided which have the structure of Formula (I):

wherein $R^1$ is halogen; and X is hydrogen or halogen, and salts thereof, which compounds are useful as anti-atherosclerotic, anti-dyslipidemic, anti-diabetic, and anti-obesity agents.

4 Claims, No Drawings

SUBSTITUTED ACID DERIVATIVES USEFUL AS ANTI-ATHEROSCLEROTIC, ANTI-DYSLIPIDEMIC, ANTI-DIABETIC AND ANTI-OBESITY AGENTS AND METHOD

CROSS-REFERENCES TO RELATED APPLICATION

This application claims priority benefit under Title 35 §119 (e) of U.S. provisional Application No. 60/819,166, filed Jul. 7, 2006, the contents of which are herein incorporated by reference in its entirety.

FIELD OF THE INVENTION

The present invention relates to novel substituted acid derivatives which modulate triglyceride levels, lipid levels, blood glucose levels, insulin levels, and non-esterified fatty acid (NEFA) levels, and thus are particularly useful in the treatment of atherosclerosis, dyslipidemia, diabetes, and obesity, and to a method for treating atherosclerosis, dyslipidemia, diabetes, especially Type 2 diabetes, as well as hyperglycemia, hyperinsulinemia, obesity, and related diseases employing such substituted acid derivatives alone or in combination with another anti-diabetic agent and/or an anti-dyslipidemic agent.

DESCRIPTION OF THE INVENTION

In accordance with the present invention, substituted acid derivatives are provided which have the structure of Formula (I):

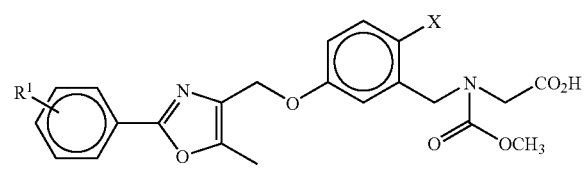

I wherein $R^1$ is halogen; and X is hydrogen or halogen, and salts thereof.

A preferred compound of the present invention has the structure of Formula (Ia):

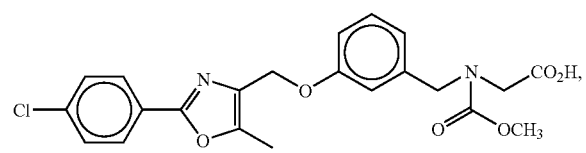

Ia and salts thereof.

Another preferred compound of the instant invention has the structure of Formula (Ib):

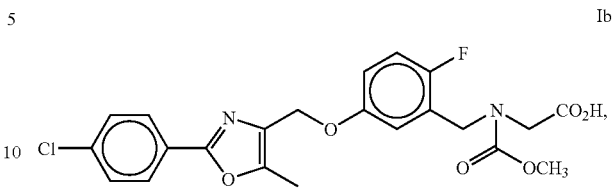

Ib and salts thereof

In addition, in accordance with the present invention, a method is provided for treating atherosclerosis, diabetes, especially Type 2 diabetes, and related diseases such as insulin resistance, hyperglycemia, hyperinsulinemia, elevated blood levels of fatty acids or glycerol, dyslipidemia, obesity, hypertriglyceridemia, inflammation, Syndrome X, diabetic complications, dysmetabolic syndrome, and related diseases wherein a therapeutically effective amount of a compound of Formula I is administered to a human patient in need of treatment.

For ease of reference, when Formula I is mentioned in the description of the invention, it is intended that Formulae Ia and Ib are also included in the scope thereof.

In addition, in accordance with the present invention, a method is provided for treating early malignant lesions (such as ductal carcinoma in situ of the breast and lobular carcinoma in situ of the breast), premalignant lesions (such as fibroadenoma of the breast and prostatic intraepithelial neoplasia (PIN), liposarcomas and various other epithelial tumors (including breast, prostate, colon, ovarian, gastric and lung), irritable bowel syndrome, Crohn's disease, gastric ulceritis, and osteoporosis and proliferative diseases such as psoriasis, wherein a therapeutically effective amount of a compound of Formula I is administered to a human patient in need of treatment.

Furthermore, in accordance with the present invention, a method is provided for treating diabetes and related diseases as defined above and hereinafter, wherein a therapeutically effective amount of a combination of a compound of Formula I and another type of anti-diabetic agent and/or a anti-dyslipidemic agent, and/or lipid modulating agent and/or other type of therapeutic agent, is administered to a human patient in need of treatment.

In the above methods of the invention, the compound of Formula I will be employed in a weight ratio to the antidiabetic agent (depending upon its mode of operation) within the range from about 0.01:1 to about 100:1, preferably from about 0.5:1 to about 10:1.

The conditions, diseases, and maladies collectively referenced to as "Syndrome X" or Dysmetabolic Syndrome are detailed in Johannsson, J. Clin. Endocrinol. Metab., 82:727-734 (1997) and other publications.

The term "diabetes and related diseases" refers to Type II diabetes, Type I diabetes, impaired glucose tolerance, obesity, hyperglycemia, Syndrome X, dysmetabolic syndrome, diabetic complications and hyperinsulinemia.

The conditions, diseases and maladies collectively referred to as "diabetic complications" include retinopathy, neuropathy and nephropathy, and other known complications of diabetes.

The term "other type(s) of therapeutic agents" as employed herein refers to one or more antidiabetic agents (other than compounds of Formula I), one or more anti-obesity agents, and/or one or more lipid-lowering agents, one or more lipid modulating agents (including anti-atherosclerosis agents), and/or one or more antiplatelet agents, one or more agents for treating hypertension, one or more anti-cancer drugs, one or more agents for treating arthritis, one or more anti-osteoporosis agents, one or more anti-obesity agents, one or more agents for treating immunomodulatory diseases, and/or one or more agents for treating anorexia nervosa.

The term "lipid-modulating" agent as employed herein refers to agents which lower LDL and/or raise HDL and/or lower triglycerides and/or lower total cholesterol and/or other known mechanisms for therapeutically treating lipid disorders.

Unless otherwise indicated, the term "lower alkyl", "alkyl" or "alk" as employed herein alone or as part of another group includes both straight and branched chain hydrocarbons, containing 1 to 20 carbons, preferably 1 to 10 carbons, more preferably 1 to 8 carbons, in the normal chain, and may optionally include an oxygen or nitrogen in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including 1 to 4 substituents such as halo, for example F, Br, Cl or I or $CF_3$, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, cycloheteroalkyl, arylheteroaryl, arylalkoxycarbonyl, heteroarylalkyl, heteroarylalkoxy, aryloxyalkyl, aryloxyaryl, alkylamido, alkanoylamino, arylcarbonylamino, nitro, cyano, thiol, haloalkyl, trihaloalkyl and/or alkylthio and/or any of the $R^3$ groups.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 10 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl,

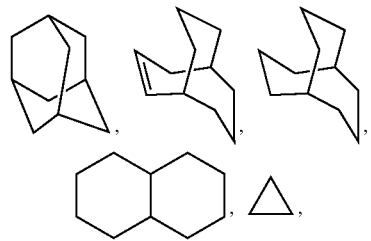

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol and/or alkylthio and/or any of the substituents for alkyl.

The term "cycloalkenyl" as employed herein alone or as part of another group refers to cyclic hydrocarbons containing 3 to 12 carbons, preferably 5 to 10 carbons and 1 or 2 double bonds. Exemplary cycloalkenyl groups include cyclopentenyl, cyclohexenyl, cycloheptenyl, cyclooctenyl, cyclohexadienyl, and cycloheptadienyl, which may be optionally substituted as defined for cycloalkyl.

The term "cycloalkylene" as employed herein refers to a "cycloalkyl" group which includes free bonds and thus is a linking group such as

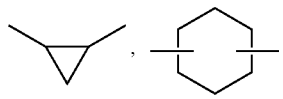

and the like, and may optionally be substituted as defined above for "cycloalkyl".

The term "alkanoyl" as used herein alone or as part of another group refers to alkyl linked to a carbonyl group.

Unless otherwise indicated, the term "lower alkenyl" or "alkenyl" as used herein by itself or as part of another group refers to straight or branched chain radicals of 2 to 20 carbons, preferably 2 to 12 carbons, and more preferably 1 to 8 carbons in the normal chain, which include one to six double bonds in the normal chain, and may optionally include an oxygen or nitrogen in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonylamino, nitro, cyano, thiol, alkylthio and/or any of the substituents for alkyl set out herein.

Unless otherwise indicated, the term "lower alkynyl" or "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, and may optionally include an oxygen or nitrogen in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, and/or any of the substituents for alkyl set out herein.

The terms "arylalkenyl" and "arylalkynyl" as used alone or as part of another group refer to alkenyl and alkynyl groups as described above having an aryl substituent.

Where alkyl groups as defined above have single bonds for attachment to other groups at two different carbon atoms, they are termed "alkylene" groups and may optionally be substituted as defined above for "alkyl".

Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

$(CH_2)_x$, $(CH_2)_m$, $(CH_2)_n$ or $(CH_2)_y$ includes alkylene, allenyl, alkenylene or alkynylene groups, as defined herein, each of which may optionally include an oxygen or nitrogen in the normal chain, which may optionally include 1, 2, or 3 substituents which include alkyl, alkenyl, halogen, cyano, hydroxy, alkoxy, amino, thioalkyl, keto, $C_3$-$C_6$ cycloalkyl, alkylcarbonylamino or alkylcarbonyloxy; the alkyl substituent may be an alkylene moiety of 1 to 4 carbons which may be attached to one or two carbons in the $(CH_2)_x$ or $(CH_2)_m$ or $(CH_2)_n$ group to form a cycloalkyl group therewith.

Examples of $(CH_2)_x$, $(CH_2)_m$, $(CH_2)_n$, $(CH_2)_y$, alkylene, alkenylene and alkynylene include

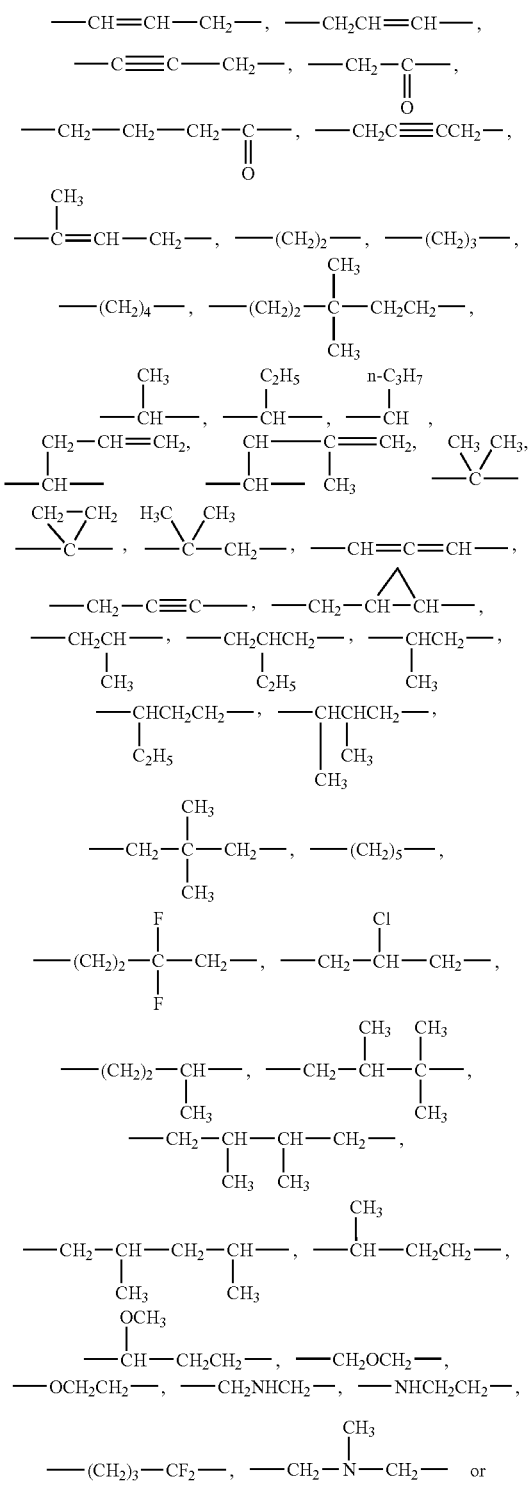

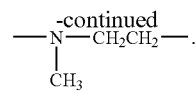

The term "halogen" or "halo" as used herein alone or as part of another group refers to chlorine, bromine, fluorine, and iodine as well as $CF_3$, with chlorine or fluorine being preferred.

The term "metal ion" refers to alkali metal ions such as sodium, potassium or lithium and alkaline earth metal ions such as magnesium and calcium, as well as zinc and aluminum.

Unless otherwise indicated, the term "aryl" or the group

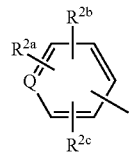

where Q is C, as employed herein alone or as part of another group refers to monocyclic and bicyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring (such as aryl, cycloalkyl, heteroaryl or cycloheteroalkyl rings for example

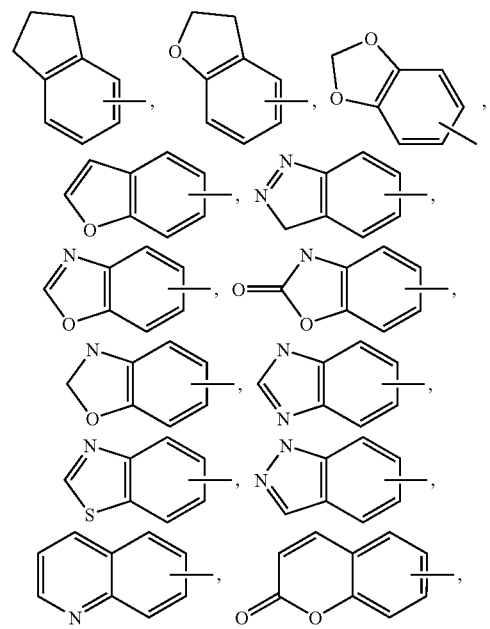

and may be optionally substituted through available carbon atoms with 1, 2, or 3 groups selected from hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, alkoxycarbonyl, arylcarbonyl, arylalkenyl, aminocarbonylaryl, arylthio, arylsulfinyl, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl and/or any of the substituents for alkyl set out herein.

Unless otherwise indicated, the term "lower alkoxy", "alkoxy", "aryloxy" or "aralkoxy" as employed herein alone or as part of another group includes any of the above alkyl, aralkyl or aryl groups linked to an oxygen atom.

Unless otherwise indicated, the term "substituted amino" as employed herein alone or as part of another group refers to amino substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl or thioalkyl. These substituents may be further substituted with a carboxylic acid and/or any of the substituents for alkyl as set out above. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, alkoxy, alkylthio, halo, trifluoromethyl or hydroxy.

Unless otherwise indicated, the term "lower alkylthio", alkylthio", "arylthio" or "aralkylthio" as employed herein alone or as part of another group includes any of the above alkyl, aralkyl or aryl groups linked to a sulfur atom.

Unless otherwise indicated, the term "lower alkylamino", "alkylamino", "arylamino", or "arylalkylamino" as employed herein alone or as part of another group includes any of the above alkyl, aryl or arylalkyl groups linked to a nitrogen atom.

Unless otherwise indicated, the term "acyl" as employed herein by itself or part of another group, as defined herein, refers to an organic radical linked to a carbonyl

group; examples of acyl groups include any of the R³ groups attached to a carbonyl, such as alkanoyl, alkenoyl, aroyl, aralkanoyl, heteroaroyl, cycloalkanoyl, cycloheteroalkanoyl and the like.

Unless otherwise indicated, the term "cycloheteroalkyl" as used herein alone or as part of another group refers to a 5-, 6- or 7-membered saturated or partially unsaturated ring which includes 1 to 2 hetero atoms such as nitrogen, oxygen and/or sulfur, linked through a carbon atom or a heteroatom, where possible, optionally via the linker $(CH_2)_p$ (where p is 1, 2 or 3), such as

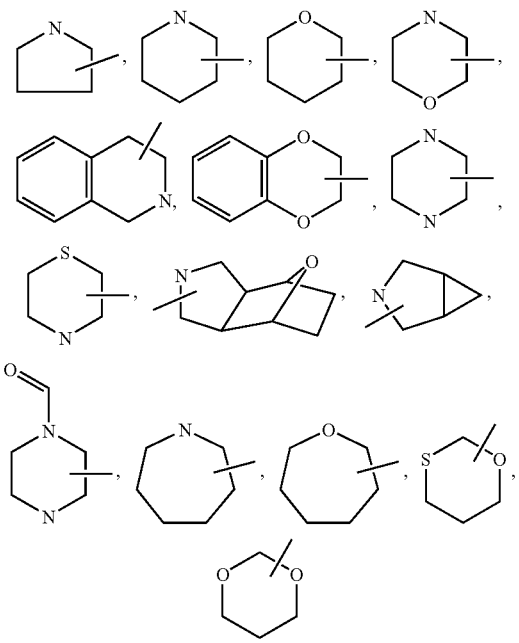

and the like. The above groups may include 1 to 4 substituents such as alkyl, halo, oxo and/or any of the substituents for alkyl or aryl set out herein. In addition, any of the cycloheteroalkyl rings can be fused to a cycloalkyl, aryl, heteroaryl or cycloheteroalkyl ring.

Unless otherwise indicated, the term "heteroaryl" as used herein alone or as part of another group refers to a 5- or 6-membered aromatic ring including

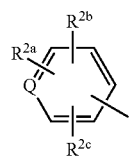

where Q is N, which includes 1, 2, 3 or 4 hetero atoms such as nitrogen, oxygen or sulfur, and such rings fused to an aryl, cycloalkyl, heteroaryl or cycloheteroalkyl ring (e.g. benzothiophenyl, indolyl), and includes possible N-oxides. The heteroaryl group may optionally include 1 to 4 substituents such as any of the substituents for alkyl or aryl set out above. Examples of heteroaryl groups include the following:

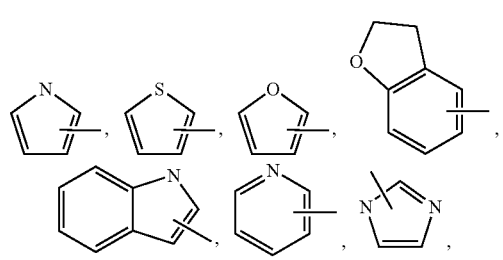

-continued

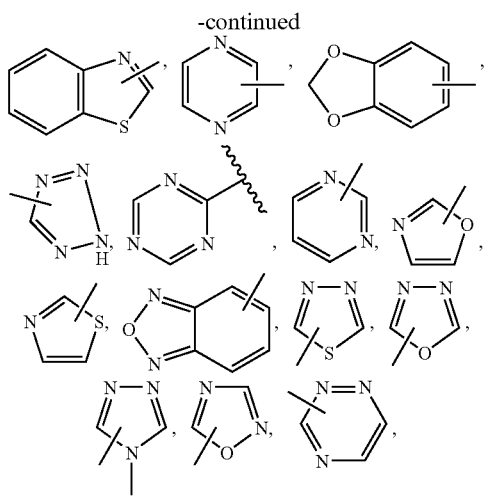

and the like.

The term "cycloheteroalkylalkyl" as used herein alone or as part of another group refers to cycloheteroalkyl groups as defined above linked through a C atom or heteroatom to a $(CH_2)_p$ chain.

The term "heteroarylalkyl" or "heteroarylalkenyl" as used herein alone or as part of another group refers to a heteroaryl group as defined above linked through a C atom or heteroatom to a —$(CH_2)_p$— chain, alkylene or alkenylene as defined above.

The term "polyhaloalkyl" as used herein refers to an "alkyl" group as defined above which includes from 2 to 9, preferably from 2 to 5, halo substituents, such as F or Cl, preferably F, such as $CF_3CH_2$, $CF_3$ or $CF_3CF_2CH_2$.

The term "polyhaloalkyloxy" as used herein refers to an "alkoxy" or "alkyloxy" group as defined above which includes from 2 to 9, preferably from 2 to 5, halo substituents, such as F or Cl, preferably F, such as $CF_3CH_2O$, $CF_3O$ or $CF_3CF_2CH_2O$.

The term "prodrug esters" as employed herein includes prodrug esters which are known in the art for carboxylic and phosphorus acid esters such as methyl, ethyl, benzyl and the like. Other prodrug ester examples of $R^4$ include the following groups:

(1-alkanoyloxy)alkyl such as,

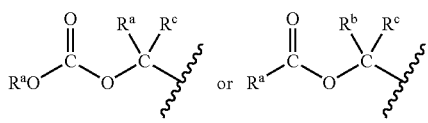

wherein $R^a$, $R^b$ and $R^c$ are H, alkyl, aryl or arylalkyl; however, $R^aO$ cannot be HO.

Examples of such prodrug esters $R^4$ include $CH_3CO_2CH_2$—, $CH_3CO_2CH_2$—$\underset{\underset{(CH_3)_2}{|}}{CH}$, t-$C_4H_9CO_2CH_2$—, or -continued $C_2H_5O\overset{\overset{O}{\|}}{C}OCH_2$—.

Other examples of suitable prodrug esters $R^4$ include

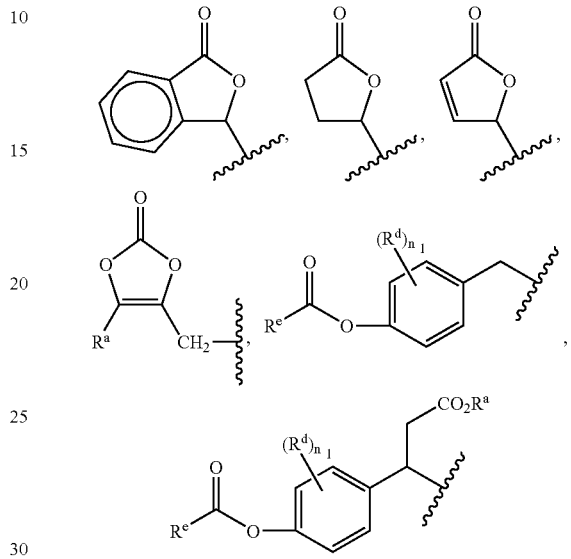

wherein $R^a$ can be H, alkyl (such as methyl or t-butyl), arylalkyl (such as benzyl) or aryl (such as phenyl); $R^d$ is H, alkyl, halogen or alkoxy, $R^e$ is alkyl, aryl, arylalkyl or alkoxyl, and $n_1$ is 0, 1 or 2.

Where the compounds of Formula I are in acid form they may form a pharmaceutically acceptable salt such as alkali metal salts such as lithium, sodium or potassium, alkaline earth metal salts such as calcium or magnesium as well as zinc or aluminum and other cations such as ammonium, choline, diethanolamine, lysine (D or L), ethylenediamine, t-butylamine, t-octylamine, tris-(hydroxymethyl)aminomethane (TRIS), N-methyl glucosamine (NMG), triethanolamine and dehydroabietylamine.

The invention may be embodied in other specific forms without departing from the spirit or essential attributes thereof. This invention also encompasses all combinations of alternative aspects of the invention noted herein. It is understood that any and all embodiments of the present invention may be taken in conjunction with any other embodiment to describe additional embodiments of the present invention. Furthermore, any elements of an embodiment may be combined with any and all other elements from any of the embodiments to describe additional embodiments.

Utilities and Combinations

Where desired, the compounds of Formula I may be used in combination with one or more anti-dyslipidemic agents or lipid-lowering agents and/or one or more other types of therapeutic agents including antidiabetic agents, anti-obesity agents, antihypertensive agents, platelet aggregation inhibitors, and/or anti-osteoporosis agents, which may be administered orally in the same dosage form, in a separate oral dosage form or by injection.

The anti-dyslipidemic agent or lipid-lowering agent which may be optionally employed in combination with the compounds of Formula I of the invention may include 1, 2, 3 or more MTP inhibitors, HMG CoA reductase inhibitors, squalene synthetase inhibitors, ACAT inhibitors, lipoxygenase inhibitors, cholesterol absorption inhibitors, ileal Na$^+$/bile acid cotransporter inhibitors, upregulators of LDL receptor activity, bile acid sequestrants, cholesterol ester transfer protein (CETP) inhibitors [e.g., torcetrapib (Pfizer) and JTT-302 (Japan Tobacco)], and/or nicotinic acid and derivatives thereof.

MTP inhibitors employed herein include MTP inhibitors disclosed in U.S. Pat. No. 5,595,872, U.S. Pat. No. 5,739,135, U.S. Pat. No. 5,712,279, U.S. Pat. No. 5,760,246, U.S. Pat. No. 5,827,875, U.S. Pat. No. 5,885,983 and U.S. application Ser. No. 09/175,180 filed Oct. 20, 1998, now U.S. Pat. No. 5,962,440. Preferred are each of the preferred MTP inhibitors disclosed in each of the above patents and applications.

All of the above U.S. patents and applications are incorporated herein by reference.

Most preferred MTP inhibitors to be employed in accordance with the present invention include preferred MTP inhibitors as set out in U.S. Pat. Nos. 5,739,135 and 5,712,279, and U.S. Pat. No. 5,760,246.

The most preferred MTP inhibitor is 9-[4-[4-[[2-(2,2,2-Trifluoroethoxy)benzoyl]amino]-1-piperidinyl]butyl]-N-(2,2,2-trifluoroethyl)-9H-fluorene-9-carboxamide

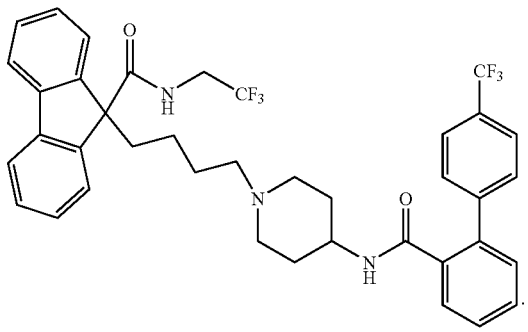

The anti-dyslipidemic agent may be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, atorvastatin disclosed in U.S. Pat. Nos. 4,681,893, 5,273,995, 5,385,929 and 5,686,104, itavastatin (Nissan/Sankyo's nisvastatin (NK-104)) disclosed in U.S. Pat. No. 5,011,930, Shionogi-Astra/Zeneca visastatin (ZD-4522) disclosed in U.S. Pat. No. 5,260,440, and related statin compounds disclosed in U.S. Pat. No. 5,753,675, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No. 0,142,146 A2, and quinoline and pyridine derivatives disclosed in U.S. Pat. Nos. 5,506,219 and 5,691,322.

In addition, phosphinic acid compounds useful in inhibiting HMG CoA reductase suitable for use herein are disclosed in GB 2205837.

The squalene synthetase inhibitors suitable for use herein include, but are not limited to, α-phosphono-sulfonates disclosed in U.S. Pat. No. 5,712,396, those disclosed by Biller et al, J. Med. Chem., 1988, Vol. 31, No. 10, pp. 1869-1871, including isoprenoid (phosphinyl-methyl)phosphonates as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C. D., Current Pharmaceutical Design, 2, 1-40 (1996).

In addition, other squalene synthetase inhibitors suitable for use herein include the terpenoid pyrophosphates disclosed by P. Ortiz de Montellano et al, J. Med. Chem., 1977, 20:243-249, the farnesyl diphosphate analog A and presqualene pyrophosphate (PSQ-PP) analogs as disclosed by Corey and Volante, J. Am. Chem. Soc., 1976, 98, 1291-1293, phosphinylphosphonates reported by McClard, R. W. et al, J.A.C.S., 1987, 109:5544 and cyclopropanes reported by Capson, T. L., PhD dissertation, June, 1987, Dept. Med. Chem. U of Utah, Abstract, Table of Contents, pp 16, 17, 40-43, 48-51, Summary.

Other anti-dyslipidemic agents suitable for use herein include, but are not limited to, probucol, and related compounds as disclosed in U.S. Pat. No. 3,674,836, probucol being preferred; bile acid sequestrants such as cholestyramine, colestipol and DEAE-Sephadex (Secholex®, Policexide®) and cholestagel (Sankyo/Geltex), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives); nicotinic acid (niacin), acipimox, acifran, neomycin, p-aminosalicylic acid, aspirin; poly(diallylmethylamine) derivatives such as disclosed in U.S. Pat. No. 4,759,923; quaternary amine poly (diallyldimethylammonium chloride) and ionenes such as disclosed in U.S. Pat. No. 4,027,009, and other known serum cholesterol lowering agents.

The anti-dyslipidemic agent may be an ACAT inhibitor such as disclosed in, Drugs of the Future 24, 9-15 (1999), (Avasimibe); "The ACAT inhibitor, Cl-1011 is effective in the prevention and regression of aortic fatty streak area in hamsters", Nicolosi et al, Atherosclerosis (Shannon, Irel). (1998), 137(1), 77-85; "The pharmacological profile of FCE 27677: a novel ACAT inhibitor with potent dyslipidemic activity mediated by selective suppression of the hepatic secretion of ApoB100-containing lipoprotein", Ghiselli, Giancarlo, Cardiovasc. Drug Rev. (1998), 16(1), 16-30; "RP 73163: a bioavailable alkylsulfinyl-diphenylimidazole ACAT inhibitor", Smith, C., et al, Bioorg. Med. Chem. Lett. (1996), 6(1), 47-50; "ACAT inhibitors: physiologic mechanisms for dyslipidemic and anti-atherosclerotic activities in experimental animals", Krause et al, Editor(s): Ruffolo, Robert R., Jr.; Hollinger, Mannfred A., Inflammation: Mediators Pathways (1995), 173-98, Publisher: CRC, Boca Raton, Fla.; "ACAT inhibitors: potential anti-atherosclerotic agents", Sliskovic et al, Curr. Med. Chem. (1994), 1(3), 204-25; "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", Stout et al, Chemtracts: Org. Chem. (1995), 8(6), 359-62, or TS-962 (Taisho Pharmaceutical Co. Ltd).

The anti-dyslipidemic agent may be an upregulator of LD2 receptor activity such as MD-700 (Taisho Pharmaceutical Co. Ltd) and LY295427 (Eli Lilly).

The anti-dyslipidemic agent may be a cholesterol absorption inhibitor preferably Schering-Plough's SCH48461 as well as those disclosed in Atherosclerosis 115, 45-63 (1995) and J. Med. Chem. 41, 973 (1998).

The anti-dyslipidemic agent may be an ileal $Na^+$/bile acid cotransporter inhibitor such as disclosed in Drugs of the Future, 24, 425-430 (1999).

The lipid-modulating agent may be a cholesteryl ester transfer protein (CETP) inhibitor such as Pfizer's CP 529,414 (WO/0038722 and EP 818448) and Pharmacia's SC-744 and SC-795.

The ATP citrate lyase inhibitor which may be employed in the combination of the invention may include, for example, those disclosed in U.S. Pat. No. 5,447,954.

Preferred anti-dyslipidemic agents are pravastatin, lovastatin, simvastatin, atorvastatin, fluvastatin, itavastatin and visastatin and ZD-4522.

The above-mentioned U.S. patents are incorporated herein by reference. The amounts and dosages employed will be as indicated in the Physician's Desk Reference and/or in the patents set out above.

The compounds of Formula I of the invention will be employed in a weight ratio to the anti-dyslipidemic agent (where present), within the range from about 500:1 to about 1:500, preferably from about 100:1 to about 1:100.

The dose administered must be carefully adjusted according to age, weight and condition of the patient, as well as the route of administration, dosage form and regimen and the desired result.

The dosages and formulations for the anti-dyslipidemic agent will be as disclosed in the various patents and applications discussed above.

The dosages and formulations for the other anti-dyslipidemic agent to be employed, where applicable, will be as set out in the latest edition of the Physicians' Desk Reference.

For oral administration, a satisfactory result may be obtained employing the MTP inhibitor in an amount within the range of from about 0.01 mg to about 500 mg and preferably from about 0.1 mg to about 100 mg, one to four times daily.

A preferred oral dosage form, such as tablets or capsules, will contain the MTP inhibitor in an amount of from about 1 to about 500 mg, preferably from about 2 to about 400 mg, and more preferably from about 5 to about 250 mg, one to four times daily.

For oral administration, a satisfactory result may be obtained employing an HMG CoA reductase inhibitor, for example, pravastatin, lovastatin, simvastatin, atorvastatin, fluvastatin or rosuvastatin in dosages employed as indicated in the Physician's Desk Reference, such as in an amount within the range of from about 1 to 2000 mg, and preferably from about 4 to about 200 mg.

The squalene synthetase inhibitor may be employed in dosages in an amount within the range of from about 10 mg to about 2000 mg and preferably from about 25 mg to about 200 mg.

A preferred oral dosage form, such as tablets or capsules, will contain the HMG CoA reductase inhibitor in an amount from about 0.1 to about 100 mg, preferably from about 0.5 to about 80 mg, and more preferably from about 1 to about 40 mg.

A preferred oral dosage form, such as tablets or capsules will contain the squalene synthetase inhibitor in an amount of from about 10 to about 500 mg, preferably from about 25 to about 200 mg.

The anti-dyslipidemic agent may also be a lipoxygenase inhibitor including a 15-lipoxygenase (15-LO) inhibitor such as benzimidazole derivatives as disclosed in WO 97/12615, 15-LO inhibitors as disclosed in WO 97/12613, isothiazolones as disclosed in WO 96/38144, and 15-LO inhibitors as disclosed by Sendobry et al "Attenuation of diet-induced atherosclerosis in rabbits with a highly selective 15-lipoxygenase inhibitor lacking significant antioxidant properties", Brit. J. Pharmacology (1997) 120, 1199-1206, and Cornicelli et al, "15-Lipoxygenase and its Inhibition: A Novel Therapeutic Target for Vascular Disease", Current Pharmaceutical Design, 1999, 5, 11-20.

The compounds of Formula I and the anti-dyslipidemic agent may be employed together in the same oral dosage form or in separate oral dosage forms taken at the same time.

The compositions described above may be administered in the dosage forms as described above in single or divided doses of one to four times daily. It may be advisable to start a patient on a low dose combination and work up gradually to a high dose combination.

The preferred anti-dyslipidemic agent is pravastatin, simvastatin, lovastatin, atorvastatin, fluvastatin or rosuvastatin as well as niacin and/or cholestagel.

The other antidiabetic agent which may be optionally employed in combination with the compound of Formula I may be 1, 2, 3 or more antidiabetic agents or antihyperglycemic agents including insulin secretagogues or insulin sensitizers, or other antidiabetic agents preferably having a mechanism of action different from the compounds of Formula I of the invention, which may include biguanides, sulfonyl ureas, glucosidase inhibitors, PPAR γ agonists, such as thiazolidinediones, dipeptidyl peptidase IV (DP4) inhibitors, SGLT2 inhibitors, and/or meglitinides, as well as insulin, and/or glucagon-like peptide-1 (GLP-1).

The other antidiabetic agent may be an oral antihyperglycemic agent preferably a biguanide such as metformin or phenformin or salts thereof, preferably metformin HCl.

Where the antidiabetic agent is a biguanide, the compounds of Formula I will be employed in a weight ratio to biguanide within the range from about 0.001:1 to about 10:1, preferably from about 0.01:1 to about 5:1.

The other antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the β-cells, with glyburide and glipizide being preferred, which may be administered in the same or in separate oral dosage forms.

The compounds of Formula I will be employed in a weight ratio to the sulfonyl urea in the range from about 0.01:1 to about 100:1, preferably from about 0.02:1 to about 5:1.

The oral antidiabetic agent may also be a glucosidase inhibitor such as acarbose (disclosed in U.S. Pat. No. 4,904, 769) or miglitol (disclosed in U.S. Pat. No. 4,639,436), which may be administered in the same or in a separate oral dosage forms.

The compounds of Formula I will be employed in a weight ratio to the glucosidase inhibitor within the range from about 0.01:1 to about 100:1, preferably from about 0.05:1 to about 10:1.

The compounds of Formula I may be employed in combination with a PPAR γ agonist such as a thiazolidinedione oral anti-diabetic agent or other insulin sensitizers (which has an insulin sensitivity effect in NIDDM patients) such as rosiglitazone (SKB), pioglitazone (Takeda), Mitsubishi's MCC-555 (disclosed in U.S. Pat. No. 5,594,016), R-119702 (Sankyo/WL), or YM-440 (Yamanouchi), preferably rosiglitazone and pioglitazone.

The compounds of Formula I will be employed in a weight ratio to the thiazolidinedione in an amount within the range from about 0.01:1 to about 100:1, preferably from about 0.05 to about 10:1.

The sulfonyl urea and thiazolidinedione in amounts of less than about 150 mg oral antidiabetic agent may be incorporated in a single tablet with the compounds of Formula I.

The compounds of Formula I may also be employed in combination with a antihyperglycemic agent such as insulin or with glucagon-like peptide-1 (GLP-1) such as GLP-1(1-36) amide, GLP-1(7-36) amide, GLP-1(7-37) (as disclosed in U.S. Pat. No. 5,614,492 to Habener, the disclosure of which is incorporated herein by reference), as well as AC2993 (Amylin) and LY-315902 (Lilly), which may be administered via injection, intranasal, inhalation or by transdermal or buccal devices.

Where present, metformin, the sulfonyl ureas, such as glyburide, glimepiride, glipyride, glipizide, chlorpropamide and gliclazide and the glucosidase inhibitors acarbose or miglitol or insulin (injectable, pulmonary, buccal, or oral) may be employed in formulations as described above and in amounts and dosing as indicated in the Physician's Desk Reference (PDR).

Where present, metformin or salt thereof may be employed in amounts within the range from about 500 to about 2000 mg per day which may be administered in single or divided doses one to four times daily.

Where present, the thiazolidinedione anti-diabetic agent may be employed in amounts within the range from about 0.01 to about 2000 mg/day which may be administered in single or divided doses one to four times per day.

Where present insulin may be employed in formulations, amounts and dosing as indicated by the Physician's Desk Reference.

Where present GLP-1 peptides may be administered in oral buccal formulations, by nasal administration or parenterally as described in U.S. Pat. No. 5,346,701 (TheraTech), U.S. Pat. Nos. 5,614,492 and 5,631,224 which are incorporated herein by reference.

The other antidiabetic agent may also be a PPAR α/γ dual agonist such as Muraglitazar (Bristol-Myers Squibb).

The antidiabetic agent may be an SGLT2 inhibitor such as disclosed in U.S. Pat. No. 6,414,126, employing dosages as set out therein. Preferred are the compounds designated as preferred in the above patent. Other suitable SGLT2 inhibitors include T-1095, phlorizin, WAY-123783, and those described in WO 01/27128, U.S. Pat. No. 6,515,117 and U.S. Pat. No. 6,414,126.

The antidiabetic agent may be a DPP4 inhibitor. These include saxagliptin (Bristol-Myers Squibb), vildagliptin (Novartis), sitagliptin (Merck) and alogliptin (Takeda) as well as those such as disclosed in WO99/38501, WO99/46272, WO99/67279 (PROBIODRUG), WO99/67278 (PROBIODRUG), WO99/61431 (PROBIODRUG), NVP-DPP728A (1-[[[2-[(5-cyanopyridin-2-yl)amino]ethyl]amino]acetyl]-2-cyano-(S)-pyrrolidine) (Novartis) as disclosed by Hughes et al, Biochemistry, 38(36), 11597-11603, 1999, TSL-225 (tryptophyl-1,2,3,4-tetrahydro-isoquinoline-3-carboxylic acid) disclosed by Yamada et al, Bioorg. & Med. Chem. Lett. 8 (1998) 1537-1540, 2-cyanopyrrolidides and 4-cyanopyrrolidides as disclosed by Ashworth et al, Bioorg. & Med. Chem. Lett., Vol. 6, No. 22, pp 1163-1166 and 2745-2748 (1996) employing dosages as set out in the above references.

The meglitinide which may optionally be employed in combination with the compound of Formula I of the invention may be repaglinide, nateglinide (Novartis) or KAD1229 (PF/Kissei), with repaglinide being preferred.

The compound of Formula I will be employed in a weight ratio to the meglitinide, PPAR-α/γ dual agonist, DP4 inhibitor or SGLT2 inhibitor within the range from about 0.01:1 to about 100:1, preferably from about 0.05 to about 10:1.

The other type of therapeutic agent which may be optionally employed with a compound of Formula I may be 1, 2, 3 or more of an anti-obesity agent including a beta 3 adrenergic agonist, a lipase inhibitor, a serotonin (and dopamine) reuptake inhibitor, a thyroid receptor agonist, a cannabinoid receptor 1 (CB-1) antagonist and/or an anorectic agent.

The beta 3 adrenergic agonist which may be optionally employed in combination with a compound of Formula I may be AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, with AJ9677, L750,355 and CP331648 being preferred.

The lipase inhibitor which may be optionally employed in combination with a compound of Formula I may be orlistat or ATL-962 (Alizyme), with orlistat being preferred.

The serotonin (and dopamine) reuptake inhibitor which may be optionally employed in combination with a compound of Formula I may be sibutramine, topiramate (Johnson & Johnson) or axokine (Regeneron), with sibutramine and topiramate being preferred.

The thyroid receptor agonist which may be optionally employed in combination with a compound of Formula I may be a thyroid receptor ligand as disclosed in WO97/21993 (U. Cal SF), WO99/00353 (KaroBio), WO 00/039077 (KaroBio), and U.S. Pat. No. 6,800,605, with compounds of the KaroBio applications and the above patent being preferred.

Cannabinoid receptor 1 antagonists and inverse agonists which may be optionally employed in combination with compounds of the present invention include rimonabant, SLV 319, and those discussed in D. L. Hertzog, Expert Opin. Ther. Patents 2004, 14, 1435-1452.

The anorectic agent which may be optionally employed in combination with a compound of Formula I may be dexamphetamine, phentermine, phenylpropanolamine or mazindol, with dexamphetamine being preferred.

The various anti-obesity agents described above may be employed in the same dosage form with the compound of Formula I or in different dosage forms, in dosages and regimens as generally known in the art or in the PDR.

The antihypertensive agents which may be employed in combination with the compound of Formula I of the invention include ACE inhibitors, angiotensin II receptor antagonists, NEP/ACE inhibitors, as well as calcium channel blockers, β-adrenergic blockers and other types of antihypertensive agents, including diuretics.

The angiotensin converting enzyme inhibitor which may be employed herein includes those containing a mercapto (—S—) moiety such as substituted proline derivatives, such as any of those disclosed in U.S. Pat. No. 4,046,889 to Ondetti et al mentioned above, with captopril, that is, 1-[(2S)-3-mercapto-2-methylpropionyl]-L-proline, being preferred, and mercaptoacyl derivatives of substituted prolines such as any of those disclosed in U.S. Pat. No. 4,316,906 with zofenopril being preferred.

Other examples of mercapto containing ACE inhibitors that may be employed herein include rentiapril (fentiapril, Santen) disclosed in Clin. Exp. Pharmacol. Physiol. 10:131 (1983); as well as pivopril and YS980.

Other examples of angiotensin converting enzyme inhibitors which may be employed herein include any of those disclosed in U.S. Pat. No. 4,374,829 mentioned above, with N-(1-ethoxycarbonyl-3-phenylpropyl)-L-alanyl-L-proline, that is, enalapril, being preferred; any of the phosphonate substituted amino or imino acids or salts disclosed in U.S. Pat. No. 4,452,790, with (S)-1-[6-amino-2-[[hydroxy-(4-phenylbutyl)phosphinyl]oxy]-1-oxohexyl]-L-proline or (ceronapril) being preferred; phosphinylalkanoyl prolines disclosed in U.S. Pat. No. 4,168,267 mentioned above with fosinopril being preferred; any of the phosphinylalkanoyl substituted prolines disclosed in U.S. Pat. No. 4,337,201; and the phosphonamidates disclosed in U.S. Pat. No. 4,432,971 discussed above.

Other examples of ACE inhibitors that may be employed herein include Beecham's BRL 36,378 as disclosed in European Patent Application Nos. 80822 and 60668; Chugai's MC-838 disclosed in C. A. 102:72588v and Jap. J. Pharmacol. 40:373 (1986); Ciba-Geigy's CGS 14824 (3-([1-ethoxycarbonyl-3-phenyl-(1S)-propyl]amino)-2,3,4,5-tetrahydro-2-oxo-1-(3S)-benzazepine-1 acetic acid HCl) disclosed in U.K. Patent No. 2103614 and CGS 16,617 (3(S)-[[(1S)-5-amino-1-carboxypentyl]amino]-2,3,4,5-tetrahydro-2-oxo-1H-1-benzazepine-1-ethanoic acid) disclosed in U.S. Pat. No. 4,473,575; cetapril (alacepril, Dainippon) disclosed in Eur. Therap. Res. 39:671 (1986); ramipril (Hoechst) disclosed in Euro. Patent No. 79-022 and Curr. Ther. Res. 40:74 (1986); Ru 44570 (Hoechst) disclosed in Arzneimittelforschung 34:1254 (1985); cilazapril (Hoffman-LaRoche) disclosed in J. Cardiovasc. Pharmacol. 9:39 (1987); R 31-2201 (Hoffman-LaRoche) disclosed in FEBS Lett. 165:201 (1984); lisinopril (Merck); indalapril (delapril) disclosed in U.S. Pat. No. 4,385,051; indolapril (Schering) disclosed in J. Cardiovasc. Pharmacol. 5:643, 655 (1983); spirapril (Schering) disclosed in Acta. Pharmacol. Toxicol. 59 (Supp. 5):173 (1986); perindopril (Servier) disclosed in Eur. J. Clin. Pharmacol. 31:519 (1987); quinapril (Warner-Lambert) disclosed in U.S. Pat. No. 4,344,949 and CI925 (Warner-Lambert) ([3S-[2 [R(*)R(*)]]3R(*)]-2-[2-[[1-(ethoxy-carbonyl)-3-phenylpropyl]amino]-1-oxopropyl]-1,2,3,4-tetrahydro-6,7-dimethoxy-3-isoquinolinecarboxylic acid HCl) disclosed in Pharmacologist 26:243, 266 (1984), WY-44221 (Wyeth) disclosed in J. Med. Chem. 26:394 (1983).

Preferred ACE inhibitors are captopril, fosinopril, enalapril, lisinopril, quinapril, benazepril, fentiapril, ramipril and moexipril.

NEP/ACE inhibitors may also be employed herein in that they possess neutral endopeptidase (NEP) inhibitory activity and angiotensin converting enzyme (ACE) inhibitory activity. Examples of NEP/ACE inhibitors suitable for use herein include those disclosed in U.S. Pat. Nos. 5,362,727, 5,366,973, 5,225,401, 4,722,810, 5,223,516, 4,749,688, 5,552,397, 5,504,080, 5,612,359, and 5,525,723, European Patent Applications 0599,444, 0481,522, 0599,444, 0595,610, 0534363A2, 534,396, 534,492, and 0629627A2.

Preferred are those NEP/ACE inhibitors and dosages thereof which are designated as preferred in the above patents/applications which U.S. patents are incorporated herein by reference; most preferred are omapatrilat, BMS 189,921 ([S—(R*,R*)]-hexahydro-6-[(2-mercapto-1-oxo-3-phenylpropyl)amino]-2,2-dimethyl-7-oxo-1H-azepine-1-acetic acid (gemopatrilat)) and CGS 30440.

The angiotensin II receptor antagonist (also referred to herein as angiotensin II antagonist or AII antagonist) suitable for use herein includes, but is not limited to, irbesartan, losartan, valsartan, candesartan, telmisartan, tasosartan or eprosartan, with irbesartan, losartan or valsartan being preferred.

A preferred oral dosage form, such as tablets or capsules, will contain the ACE inhibitor or AII antagonist in an amount within the range from abut 0.1 to about 500 mg, preferably from about 5 to about 200 mg and more preferably from about 10 to about 150 mg.

For parenteral administration, the ACE inhibitor, angiotensin II antagonist or NEP/ACE inhibitor will be employed in an amount within the range from about 0.005 mg/kg to about 10 mg/kg and preferably from about 0.01 mg/kg to about 1 mg/kg.

Where a drug is to be administered intravenously, it will be formulated in conventional vehicles, such as distilled water, saline, Ringer's solution or other conventional carriers.

It will be appreciated that preferred dosages of ACE inhibitor and AII antagonist as well as other antihypertensives disclosed herein will be as set out in the latest edition of the Physician's Desk Reference (PDR).

Other examples of preferred antihypertensive agents suitable for use herein include omapatrilat (Vanlev®), amlodipine besylate (Norvasc®), prazosin HCl (Minipress®), verapamil, nifedipine, nadolol, diltiazem, felodipine, nisoldipine, isradipine, nicardipine, atenolol, carvedilol, sotalol, terazosin, doxazosin, propranolol, and clonidine HCl (Catapres®).

Diuretics which may be employed in combination with compounds of Formula I include hydrochlorothiazide, torasemide, furosemide, spironolactono, and indapamide.

Antiplatelet agents which may be employed in combination with compounds of Formula I of the invention include aspirin, clopidogrel, ticlopidine, dipyridamole, abciximab, tirofiban, eptifibatide, anagrelide, and ifetroban, with clopidogrel and aspirin being preferred.

The antiplatelet drugs may be employed in amounts as indicated in the PDR. Ifetroban may be employed in amounts as set out in U.S. Pat. No. 5,100,889.

Antiosteoporosis agents suitable for use herein in combination with the compounds of Formula I of the invention include parathyroid hormone or bisphosphonates, such as MK-217 (alendronate) (Fosamax®). Dosages employed will be as set out in the PDR.

In carrying out the method of the invention, a pharmaceutical composition will be employed containing the compounds of Formula I, with or without another therapeutic agent, in association with a pharmaceutical vehicle or diluent. The pharmaceutical composition can be formulated employing conventional solid or liquid vehicles or diluents and pharmaceutical additives of a type appropriate to the mode of desired administration. The compounds can be administered to mammalian species including humans, monkeys, dogs, etc. by an oral route, for example, in the form of tablets, capsules, granules or powders, or they can be administered by a parenteral route in the form of injectable preparations. The dose for adults is preferably between 0.1 and 2,000 mg per day, which can be administered in a single dose or in the form of individual doses from 1-4 times per day. Alternatively, another preferred mode of administration may be intermittent dosing (i.e., a single dose of drug administered at intervals, ranging from once every 2 days to once every 7 days).

A typical capsule for oral administration contains compounds of Formula I (25 mg), lactose (7.5 mg) and magnesium stearate (1.5 mg). The mixture is passed through a 60 mesh sieve and packed into a No. 1 gelatin capsule.

The following Examples represent preferred embodiments of the invention.

Abbreviations

For ease of reference, the following abbreviations are employed herein, including the methods of preparation and in the Examples that follow:
aq.=aqueous
Ar=argon
Bn=benzyl
Boc=tert-butoxycarbonyl
$BBr_3$=boron tribromide
Cbz=carbobenzyloxy or carbobenzoxy or benzyloxycarbonyl
Cbz-Cl=benzyl chloroformate
$CH_2Cl_2$=dichloromethane
DCE=1,2 dichloroethane
DIBALH=diisobutyl aluminum hydride
DMAP=4-dimethylaminopyridine
DME=1,2 dimethoxyethane
DMF=dimethyl formamide
DMSO=dimethyl sulfoxide
EDC (or EDC.HCl) or EDCI (or EDCI.HCl) or EDAC=3-ethyl-3'-(dimethylamino)propyl-carbodiimide hydrochloride (or 1-(3-dimethylaminopropyl)-3-ethylcarbodiimide hydrochloride)
Et=ethyl
$Et_2O$=diethyl ether
$Et_3N$=triethylamine
EtOAc=ethyl acetate
EtOH=ethanol
FMOC=fluorenylmethoxycarbonyl
g=gram(s)
h or hr=hour(s)
hex=hexanes
HMPA=hexamethyl phosphoric triamide
HOAc or AcOH=acetic acid
HPLC=high performance liquid chromatography
HRMS=high resolution mass spectrometry
i-$Pr_2$NEt=diisopropylethylamine
i-PrOH=isopropanol
ISCO=The Teledyne Isco Chromatography instrument is used for purification of organic compounds using silica gel and organic solvents under medium pressure with automatic fraction collectors using UV detection.
$K_2CO_3$=potassium carbonate
Kg=kilogram(s)
KOH=potassium hydroxide
L=liter
LC/MS=high performance liquid chromatography/mass spectrometry
$LiAlH_4$=lithium aluminum hydride
LiOH=lithium hydroxide
LRMS=low resolution mass spectrometry
Me=methyl
MeCN=acetonitrile
MeOH=methanol
meq=milliequivalent
mg=milligram(s)
$MgSO_4$=magnesium sulfate
min=minute(s)
mL=milliliter
mmol=millimole(s)
mol=moles
mp=melting point
MS or Mass Spec=mass spectrometry
$N_2$=nitrogen
$NaBH(OAc)_3$=sodium triacetoxyborohydride
$NaBH_4$=sodium borohydride
$NaHCO_3$=sodium bicarbonate
$NaN(TMS)_2$=sodium hexamethyldisilazide or sodium bis(t-rimethylsilyl)amide
NaOH=sodium hydroxide
NMM=N-methyl morpholine
NMR=nuclear magnetic resonance
NMR spectral data: s=singlet; d=doublet; m=multiplet; br=broad; t=triplet
Pd/C=palladium on carbon
Ph=phenyl
$Ph_3P$=triphenylphosphine
RT=room temperature
sat or sat'd=saturated
$SiO_2$=silica gel
TBS=tert-butyldimethylsilyl
t-Bu=tertiary butyl
TFA=trifluoroacetic acid
THF=tetrahydrofuran
TLC=thin layer chromatography
TMS=trimethylsilyl
μL=microliter

EXAMPLES

Methods of Preparation

The compounds of Formula (I) may generally be prepared according to the following general synthetic reaction schemes as well as relevant published literature procedures that may be used by one skilled in the art. Exemplary reagents, procedures and conditions for these reactions appear hereinafter and in the working examples. Starting materials are commercially available or can be readily prepared by one of ordinary skill in the art using known methods. Unless otherwise specified the various substituents of the compounds are defined in the same manner as the Formula I.

Schemes

Schemes 1-3 describe a general synthetic sequence for the preparation of the compounds of Formula I. During the preparation of compounds of Formula I, one or more protecting groups might be used; reaction conditions for protection and deprotection may be found in the "Protective Groups in Organic Synthesis", $3^{rd}$ Edition, T. W. Greene and P. G. M. Wuts, John Wiley and Sons Inc, 1999, or other methods used by one of ordinary skill in the art.

The syntheses of compounds of Formula I (including Ia and Ib) can be accomplished via the convergent route outlined in Schemes 1 and 2. The synthesis of the key intermediate, the 4-chloromethyl 2-para-chloro-phenyloxazole IV, is optimally achieved in a one-pot, two step procedure from 2,3-butanedione mono-oxime and p-chlorobenzaldehyde involving HCl-mediated condensation, followed by dehydrative chlorination with acetyl chloride (Scheme 1). An alternative synthesis utilizes $POCl_3$ to perform the dehydrative chlorination of III to IV.

SCHEME 1

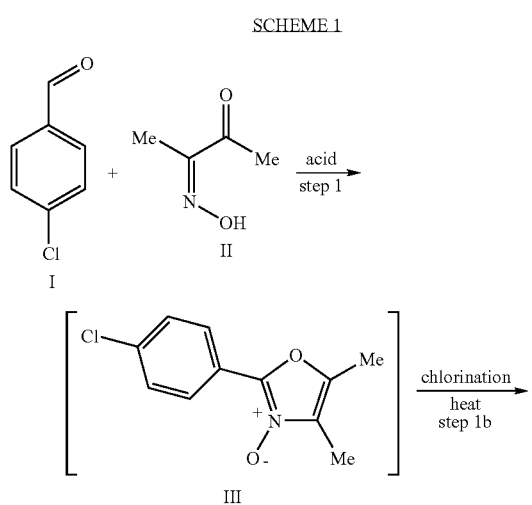

Intermediate IV is then used as shown in Scheme 2 below. Starting from 3-hydroxybenzaldehydes V and glycine methyl ester hydrochloride VI, the corresponding imines are formed by condensation in the presence of base. These imines can then be reduced in situ to the secondary amines VII. Amines VII give the methyl carbamates VIII after treatment with dimethyl dicarbonate and base. Alternatively, treatment of amines VII with methyl chloroformate under Schotten-Baumann conditions also proceed in comparable yield. Phenols VIII can be reacted with the chloromethyl-oxazole IV in the presence of base to give the methyl esters IX. Hydrolysis of esters IX with aqueous base gives compounds of Formula I.

SCHEME 2

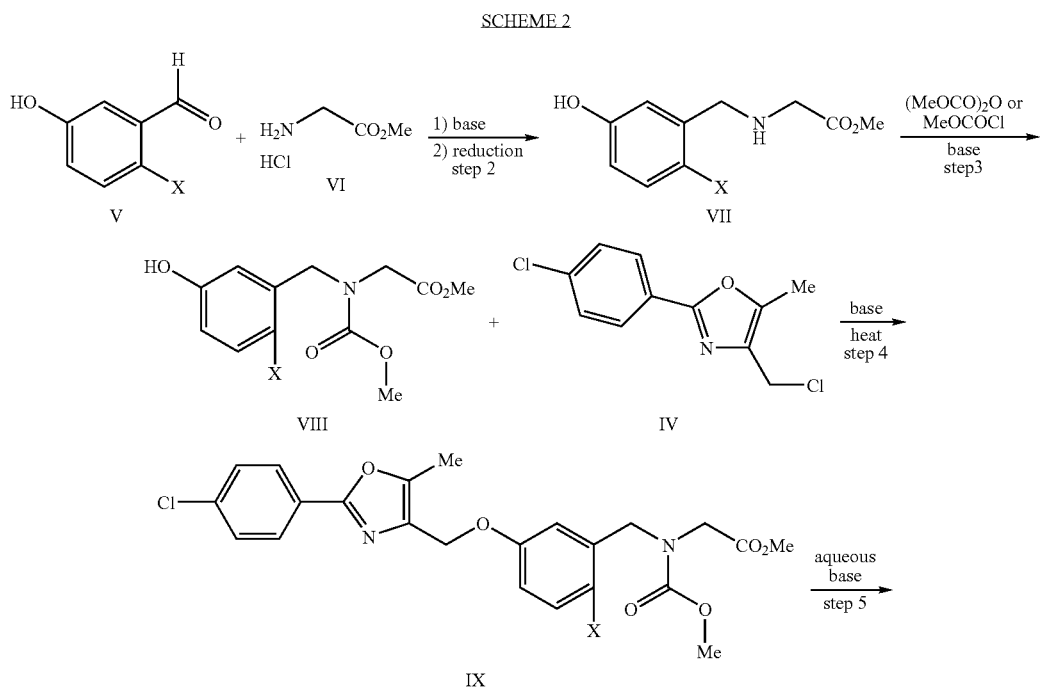

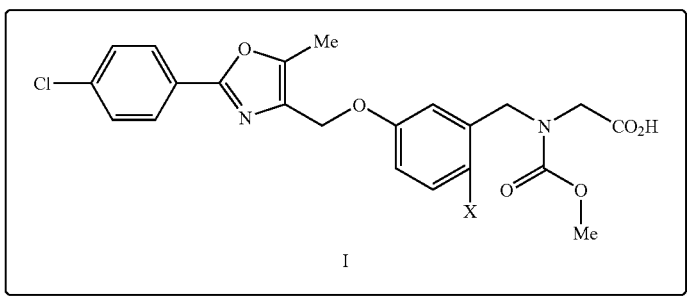

The synthesis of compounds of Formula I can alternatively be accomplished via the route outlined in Scheme 3. The 3-hydroxybenzaldehydes V can be alternatively derived from substituted ethers X by deprotection methods known in the art. The phenols V can be treated first with the chloromethyl-oxazole intermediate IV and base to give the phenyloxazole benzaldehydes XI. Imine formation from benzaldehydes XI and glycine methyl ester hydrochloride VI, followed by in situ reduction gives the secondary amines XII. Methyl carbamate formation from amines XII as described in Scheme 2 provides the methyl esters IX. Hydrolysis of esters IX with aqueous base gives compounds of Formula I.

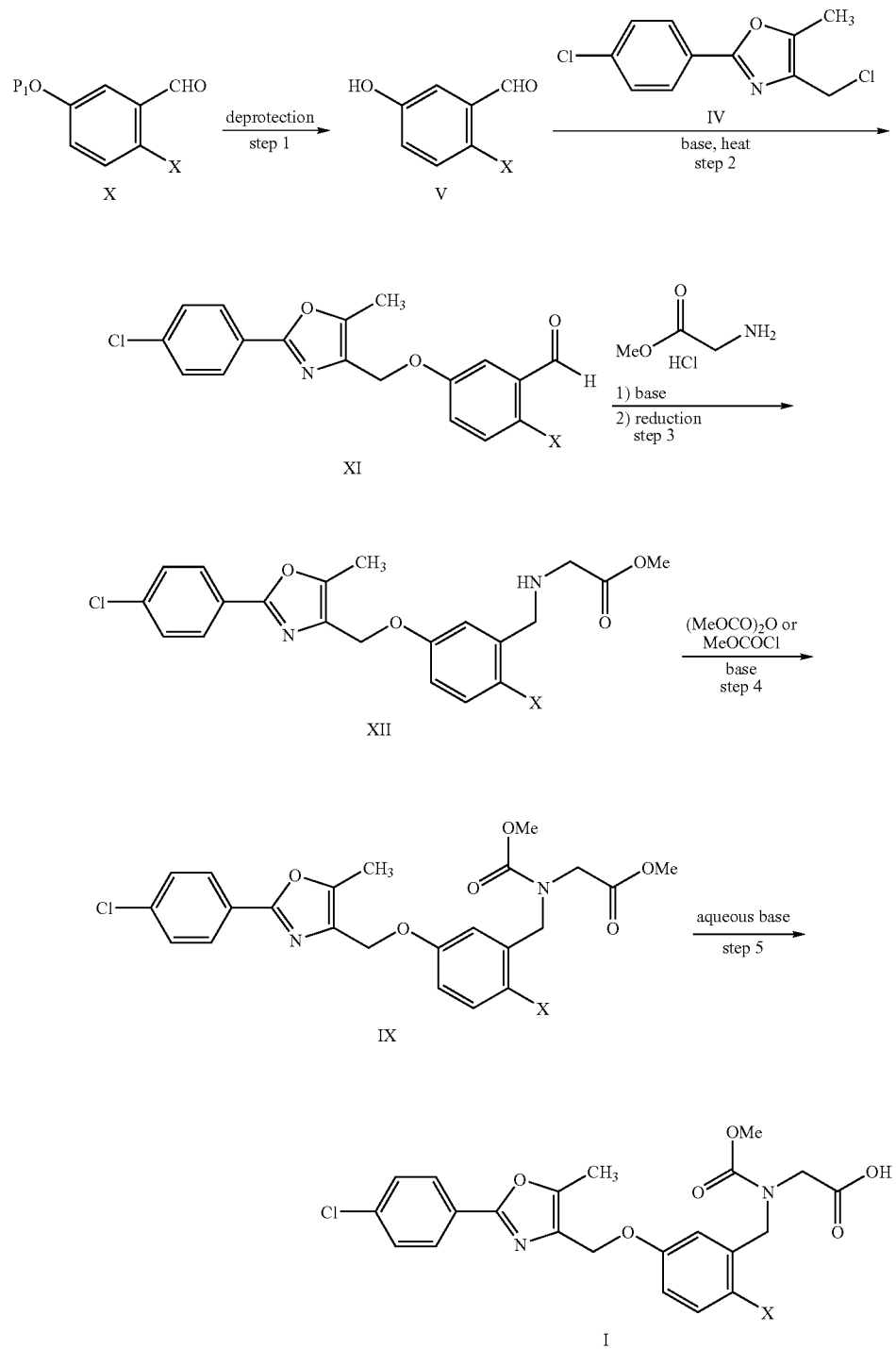

Detailed Description of Procedures

The experimental procedures are described below. Where indicated, detailed spectroscopic and physical characterization of intermediates was performed on purified samples from previous syntheses of the Examples.

Example 1

Glycine, N-[[3-[[2-(4-chlorophenyl)-5-methyl-4-oxazolyl]methoxy]phenyl]methyl]-N-(methoxycarbonyl)-

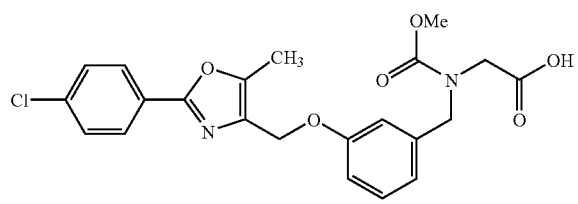

Synthesis of 1a: 4-(Chloromethyl)-5-methyl-2-[4-chlorophenyl]oxazole

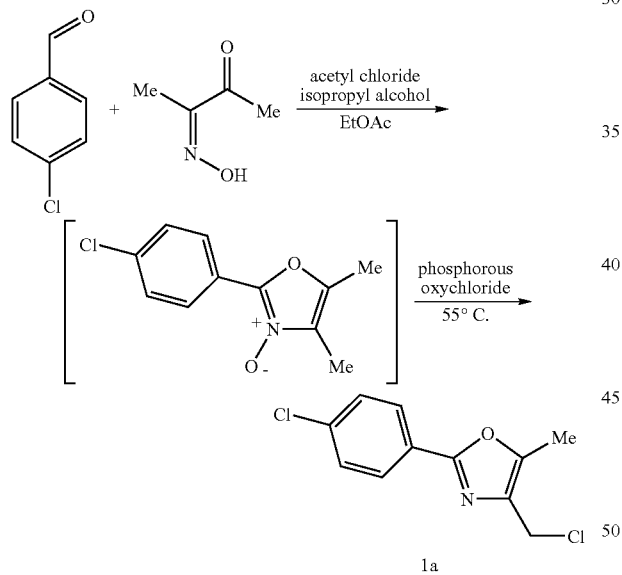

To a white slurry of 4-chlorobenzaldehyde (150.0 g, 1070 mmol) and 2,3-butanedione monoxime (102.5 g, 1010 mmol) in EtOAc (600 mL) at 0° C. under $N_2$ was bubbled gaseous HCl for 20 min. The reaction mixture was stirred at RT under $N_2$ for 40 h, then was concentrated in vacuo to a volume of ~400 mL, and stirred at 0° C. for 45 min. The resulting slurry was filtered and the filtrate was washed with cold EtOAc (5×100 mL) to give the intermediate N-oxide (228.5 g) as a solid. This material was dissolved in $CHCl_3$ (900 mL), and $POCl_3$ (128 mL, 1378 mmol) was slowly added over 25 min. The mixture was heated to 55° C. for 2.5 h, then was cooled to RT and concentrated in vacuo. The syrup was dissolved in EtOAc (1 L) and cooled with an ice water bath. Saturated aqueous $NaHCO_3$ (750 mL) was slowly added over 5 min to the reaction solution while the temperature was kept at <15° C. The pH was then adjusted to ~6 by adding solid $Na_2CO_3$ (191 g). The aqueous layer was extracted with EtOAc (300 mL). The combined organic layers were dried ($Na_2SO_4$) and concentrated in vacuo to give the crude oxazole chloride 1a (212 g) which was dissolved in 4:1 $CH_2Cl_2$/heptane (375 mL), and filtered through a pad of silica gel (400 mL). After volatiles were removed in vacuo, the residue was crystallized from $CH_2Cl_2$/heptane (600 mL, ⅔) to afford the desired oxazole chloride 1a (189.7 g, 77.3%) as a white solid. $^1$H NMR ($CDCl_3$) δ 7.91 (d, 2H, J=8.8 Hz), 7.38 (d, 2H, J=8.7 Hz), 4.52 (s, 2H), 2.39 (s, 3H) ppm; $^{13}$C NMR ($CDCl_3$) δ 159.0, 146.8, 136.3, 133.0, 129.0 (2C), 127.4 (2C), 125.6, 37.1, 10.3; HRMS for $C_{11}H_9Cl_2NO$, Calcd for (M+H)$^+$: 242.0139, Found: 242.0135.

Alternative Synthesis of 1a

To a stirred mixture of 4-chlorobenzaldehyde (7.0 g, 49.7 mmol), 2,3-butanedione monoxime (5.05 g, 49.9 mmol) in EtOAc (35 mL) and iPrOH (18 mL) was added acetyl chloride (21.3 mL) dropwise over 15 min at 0° C. under $N_2$. The reaction mixture was stirred at 0° C. for 30 min, then was warmed to RT and stirred at RT for an additional 2 h. More acetyl chloride (10 mL) was added dropwise over 5 min at RT, after which the mixture was heated to 55° C. for 45 min. The reaction was cooled to RT, and quenched into saturated aqueous $K_2CO_3$ (50 mL). The organic layer was separated and the aqueous layer was extracted with EtOAc (2×30 mL). The combined organic extracts were dried ($Na_2SO_4$) and concentrated in vacuo to give the crude product (12.5 g) which was recrystallized from i-PrOH to give the desired oxazole chloride 1a (11.8 g, 97%) as a white solid. HRMS m/e 242.0132 (M$^+$); Elemental analysis calculated for $C_{11}H_9Cl_2NO$: C, 54.57%; H, 3.74%; N, 5.78%. Found: C, 54.66%; H, 3.59%; N, 5.70%.

Synthesis of 1b

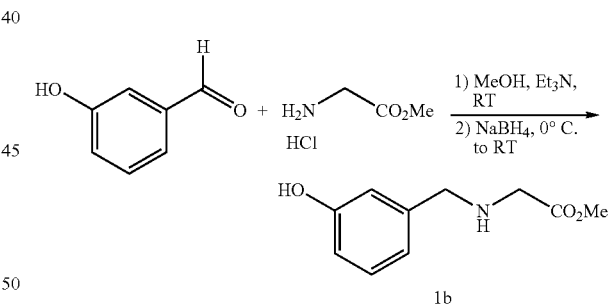

To a RT solution of glycine methyl ester hydrochloride (84.86 g, 0.67 mol) in MeOH (900 mL) was added $Et_3N$ (68.29 g, 0.675 mol). After 15 min, a solution of 3-hydroxybenzaldehyde (75 g, 0.614 mol) in MeOH (500 mL) was added. After stirring for 1 h at RT, the reaction mixture was cooled to 0° C., and $NaBH_4$ (5.7 g, 150 mmol) was then added portion-wise over 20 min (temperature maintained at ≦25° C.). After stirring 1 h, volatiles were removed in vacuo at 45-50° C. from the reaction mixture. The resulting residue was partitioned between EtOAc (500 mL) and water (500 mL). The aqueous layer was extracted with EtOAc (200 mL). The combined organic extracts were washed with brine, dried ($Na_2SO_4$), then concentrated in vacuo to afford the desired amino-ester 7 as a pale yellow solid (113.9 g, 95%), which was used in the next step without further purification.

Material purified from a previous batch: $^1$H-NMR (CDCl$_3$, 400 MHz) δ7.16 (m, 1H), 6.82 (m, 1H), 6.78 (s, 1H), 6.72 (m, 1H), 3.73 (m, 4H), 3.43 (s, 3H);

Synthesis of 1c:
[(3-Hydroxy-benzyl)-methoxycarbonyl-amino]-acetic Acid Methyl Ester

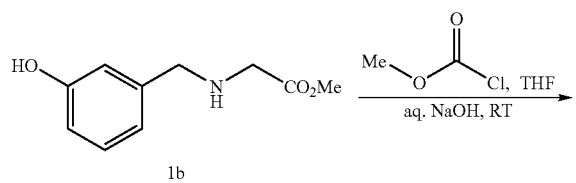

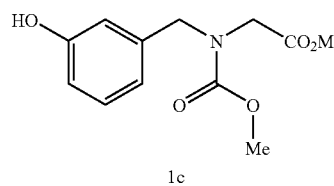

To a stirred 0° C. solution of compound 1b (65.0 g, 333 mmol) in THF (325 mL) and saturated aqueous NaHCO$_3$ (260 mL) was added dropwise methyl chloroformate (25.7 mL, 333 mmol) over 20 min under N$_2$. The mixture was stirred at 0° C. for 45 min, then was extracted with EtOAc (2×260 mL). The combined organic extracts were dried (Na$_2$SO$_4$) and concentrated in vacuo to give the crude carbamate-ester 8 (83.8 g, 99.4%) as a yellow oil. This material was used directly in the next step without further purification. $^1$H-NMR (CDCl$_3$, 400 MHz) δ7.19 (m, 1H), 6.78 (m, 3H), 6.14 (br. s, 1H), 4.54 (d, 2H, J=5.6 Hz), 3.98 (s, 1H), 3.90 (s, 1H), 3.80 (d, 3H, J=13.2 Hz), 3.73 (d, 3H, J=4.8 Hz).

Alternate Synthesis of 1c

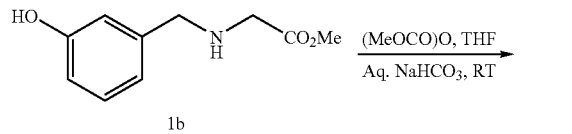

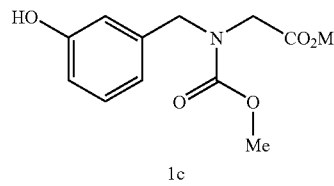

To a solution of Example 1b compound (9.76 g, 50.0 mmol) in THF (100 mL) was added 1 M aqueous NaHCO$_3$ (105 mL, 105 mmol). With vigorous stirring, dimethyl dicarbonate (5.63 mL, 52.5 mmol) was added dropwise over ~2 min at RT. After 20 min, the reaction mixture was extracted with twice with EtOAc. The combined organic extracts were dried (Na$_2$SO$_4$), then concentrated in vacuo. The resulting pale-yellow residue was chromatographed (SiO$_2$; 330 g column, continuous gradient from 0-100% EtOAc in hexanes over 20 min, flow rate=80 mL/min, ISCO chromatography system), to provide Example 1c as a clear, colorless viscous oil (9.0 g, 71%).

Synthesis of 1d: Methyl ({3-[2-(4-chloro-phenyl)-5-methyl-oxazol-4-ylmethoxy]-benzyl}-methoxycarbonyl-amino)-acetic acid methyl ester

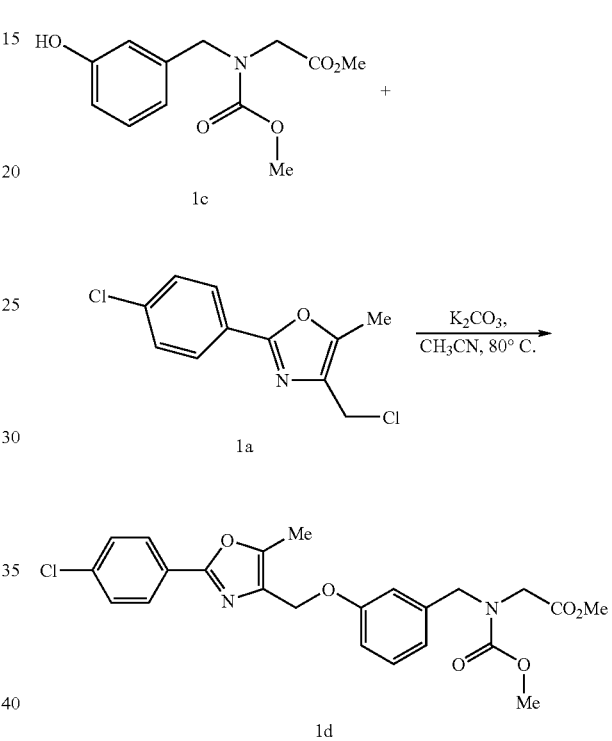

To a solution of example 1c (83.8 g, 331 mmol) in MeCN (700 mL) was added example 1a (80.1 g, 331 mmol) and anhydrous K$_2$CO$_3$ (137 g, 993 mmol). The mixture was heated at 70° C. for 21 h under N$_2$, then was cooled to 5° C. and poured into saturated aqueous NH$_4$Cl (1 L), and extracted with EtOAc (400 mL). The organic layer was dried (Na$_2$SO$_4$), and concentrated in vacuo to yield the carbamate ester (155.8 g) as a yellow syrup, which was chromatographed (2.5 kg SiO$_2$, elution with a gradient from 20 to 50% EtOAc in heptane) to give the desired carbamate-ester 1d (108.1 g, 70.7%) as a colorless solid. mp 83.4° C. $^1$H-NMR (CDCl$_3$, 400 MHz) δ7.97 (m, 2H), 7.42 (d, 2H, J=8.4 Hz), 7.28 (m, 1H), 6.89 (m, 3H), 4.98 (s, 2H), 4.56 (d, 2H, J=12.0 Hz), 3.97 (s, 1H), (3.88 (s, 1H), 3.76 (d, 3H, J=15.2 Hz), 3.73 (d, 3H, J=1.2 Hz), 2.45 (s, 3H); $^{13}$C-NMR (CDCl$_3$, 100 MHz) δ170.5, 170.4, 159.5, 159.3, 159.2, 157.5, 157.3, 147.8, 138.9, 136.6, 136.6, 132.5, 130.2, 130.1, 129.4, 127.8, 126.3, 126.3, 121.4, 120.7, 114.9, 114.6, 114.3, 114.1, 62.5, 53.6 (2 signals; rotamers), 52.5, 51.7, 51.4, 48.1, 47.6, 10.9; HRMS m/e 459.1323 (M+); Elemental analysis calculated for C$_{23}$H$_{23}$ClN$_2$O$_6$: C, 60.20%; H, 5.05%; N, 6.10%. Found: C, 60.41%; H, 5.08%; N, 6.00%.

Synthesis of Example 1

Glycine, N-[[3-[[2-(4-chlorophenyl)-5-methyl-4-oxazolyl]methoxy]phenyl]methyl]-N-(methoxycarbonyl)-

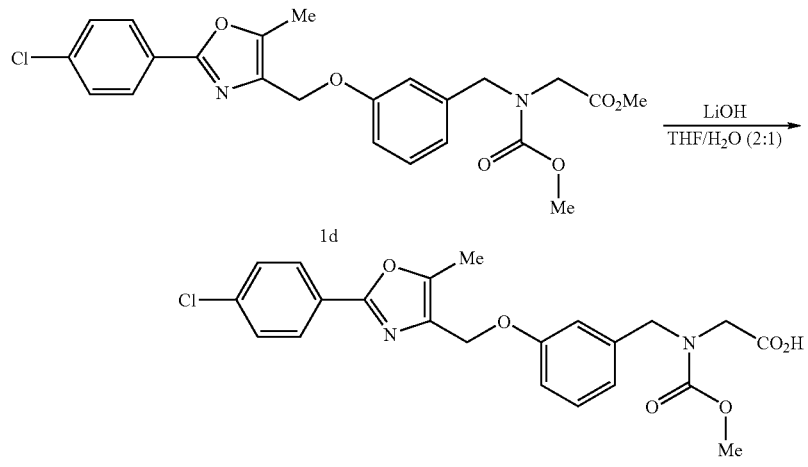

Example 1

To a stirred solution of methyl ester 1d (108 g, 235 mmol) in THF (732 mL) and water (366 mL) was added LiOH.H$_2$O (24.6 g, 585.9 mmol). The mixture was stirred at RT under N$_2$ for 2 h and diluted with EtOAc (200 mL). The solution was acidified to pH=2 by the addition of aqueous 1N HCl. The organic layer was separated and the aqueous layer was extracted with EtOAc (2×250 mL). The combined organic extracts were washed with water (2×150 mL), dried (Na$_2$SO$_4$), and concentrated in vacuo to give crude acid Example 1 (97 g, 93%). HPLC analysis showed that the purity of this batch was 98.5%.

Recrystallization: Crude acid Example 1 (210 g, material combined from several batches) was dissolved in hot EtOAc (1.2 L) at 78° C., then was cooled to RT over 60 min, then further cooled to 5° C. The slurry was stirred at 5° C. for 40 min and filtered. The solid filter cake was washed with cold EtOAc (2×100 mL). The colorless solid was dried in vacuo at 55° C. for 8 h until a constant weight was obtained. The weight of the purified Example 1 compound was 191 g (91% recovered yield). The chemical purity was determined to be 99.9% by analytical HPLC.

$^1$H NMR (DMSO-d6; 500 MHz, 19.8° C.) δ 12.72 (s, 1H), 7.93 (d, J=8.8 Hz, 2H), 7.57 (d, J=8.8 Hz, 2H), 7.26 (m, 1H), 6.94 (m, 2H), 6.86 (m, 1H), 4.98 (s, 2H), 4.42 (d, J=4.4 Hz, 2H), 3.84 (d, J=4.9 Hz, 2H), 3.60 (d, J=7.4 Hz, 3H) 2.43 (s, 3H).

$^1$H NMR (DMSO-d6; 500 MHz, 65° C.) δ 12.47 (s, 1H), 7.93 (d, J=8.79 Hz, 2H), 7.56 (d, J=8.35 Hz, 2H), 7.25 (t, J=8.13 Hz, 13H), 6.91-6.98 (m, 2H), 6.86 (d, J=7.47 Hz, 2H), 4.44 (s, 2H), 3.85 (s, 2H), 3.62 (s, 3H), 2.43 (s, 3H).

$^{13}$C NMR (DMSO-d6; 126 MHz, 19.8° C.) δ 170.7, 170.6, 158.2, 157.9, 156.4, 147.8, 139.2, 135.0, 132.1, 129.2, 127.3, 125.6, 120.1, 119.7, 114.0, 113.4, 61.1, 52.6, 51.0, 50.6, 48.4, 47.9, 39.5, 9.9 (note: extra peaks due to rotamers as the spectrum was run at 19.8° C.).

HRMS(M+H)$^+$=445.1173 (Δ=1.4 ppm).

Example 2

Glycine, N-[[3-[[2-(4-chlorophenyl)-5-methyl-4-oxazolyl]methoxy]5-fluorophenyl]methyl]-N-(methoxycarbonyl)-

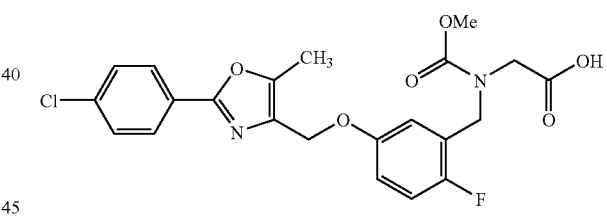

a.

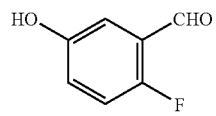

To a −78° C. solution of 2-fluoro-5-methoxybenzaldehyde (16.2 g, 105.2 mmol) in dry CH$_2$Cl$_2$ (60 mL) was added BBr$_3$ (126.2 mL of a 1.0 M solution in CH$_2$Cl$_2$, 126.2 mmol) dropwise over 5 min. The reaction was allowed to warm to 0° C. and stirred at 0° C. for 4 h, (at this point HPLC/LCMS indicated that starting material had been completely consumed), then was cooled to −78° C. CH$_2$Cl$_2$ (200 mL) and water (100 mL) were added cautiously to quench the reaction, which was then warmed to RT. The organic layer was separated, and the aqueous layer was extracted with CH$_2$Cl$_2$ (3×200 mL). The combined organic extracts were dried (MgSO$_4$) and concentrated in vacuo to afford a brown residue, which was chromatographed (120 g SiO₂ ISCO column; continuous gradient from 1:99 to 40:60 EtOAc:hexanes) to give compound 2a (14 g) as a brown solid. Spectra data for 2a: ¹H NMR (CDCl₃) δ 10.22 (s, 1H), 7.27-7.45 (m, 2H), 7.11-7.15 (m, 1H), 7.02 (t, 1H, J=9.4 Hz) ppm; ¹⁹F NMR (CDCl3) δ −131.95 ppm; ¹³C NMR (CDCl₃) δ 188.66 (d, J=5.1 Hz), 159.43 (d, J=251.8 Hz), 152.55, 124.44 (d, J=10.2 Hz), 123.90 (d, J=7.6 Hz), 117.65 (d, J=12.9 Hz), 113.15 ppm; LRMS for C₇H₅FO₂: (M+H)⁻=141 b. 5-((2-(4-Chlorophenyl)-5-methyloxazol-4-yl)methoxy)-2-fluorobenzaldehyde 3

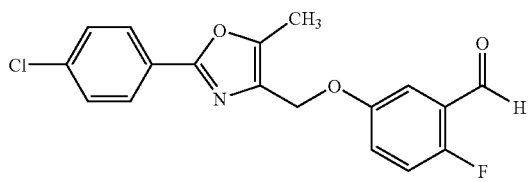

A solution of Example 2a compound (4.0 g, 28.6 mmol), Example 1a compound (6.89 g, 28.6 mmol) and K₂CO₃ (11.84 g, 85.8 mmol) in MeCN (50 mL) was heated at 80° C. under N₂ for 6 h, at which point HPLC analysis indicated that the reaction was complete. The reaction was cooled to RT. CH₂Cl₂ (50 mL) was added and the mixture was stirred for 5 min, then was filtered. The solid was washed with CH₂Cl₂ (20 mL). The combined filtrates were concentrated in vacuo; the residue was chromatographed (SiO₂; 120 g ISCO column; continuous gradient from 1-40% EtOAc in hexanes) to give Example 2b compound (9.76 g; 99%) as a white solid. ¹H NMR (CDCl₃) δ 10.29 (s, 1H), 7.89 (d, 2H, J=8.8 Hz), 7.42 (dd, 1H, J=5.3, 3.6 Hz), 7.35 (d, 2H, J=8.3 Hz), 7.19-7.22 (m, 1H), 7.06 (t, 1H, J=9.3 Hz), 4.94 (s, 2H), 2.41 (s, 3H) ppm; ¹⁹F NMR (CDCl₃) δ −131.71 ppm; ¹³C NMR (CDCl₃) δ 186.7 (d, J=7.6 Hz), 159.6 (d, J=254.3 Hz), 159.1, 154.7, 147.5, 136.1, 131.5, 128.9 (2C), 127.3 (2C), 125.7, 124.5 (d, J=10.2 Hz), 124.0 (d, J=10.2 Hz), 117.5 (d, J=22.9 Hz), 111.0, 62.5, 10.4; LRMS for C₁₈H₁₃ClFNO₃: (M+H)⁺=346.

c. Methyl 2-(5-((2-(4-chlorophenyl)-5-methyloxazol-4-yl)methoxy)-2-fluorobenzylamino)acetate

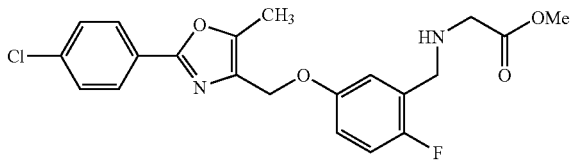

To the above 2b compound (9.76 g; 28.3 mmol) in dry MeOH (50 mL) was added glycine methyl ester hydrochloride (4.31 g, 34.3 mmol) and Et₃N (5.17 ml, 37.2 mmol), and the mixture was stirred under N₂ at RT overnight. The reaction was then cooled to −5° C. and NaBH₄ (1.41 g, 37.3 mmol) was added portionwise. The reaction was stirred at 0° C. for 30 min, then was warmed to RT over 30 min. MeOH (5 mL) was then added dropwise at 0° C. to quench the reaction. The mixture was concentrated in vacuo. The residue was partitioned between EtOAc (100 mL) and water (20 mL). The organic phase was washed with brine (20 mL), dried (MgSO₄), and concentrated in vacuo. The residue was chromatographed (SiO₂; 120 g ISCO column; continuous gradient from 0 to 100% EtOAc in hexanes) to afford Example 2c compound (8.5 g; 72% yield from Example 2a compound).

¹H NMR (CDCl₃, N—H proton not located) δ 7.95 (d, 2H, J=8.8 Hz), 7.42 (d, 2H, J=8.8 Hz), 7.03 (dd, 1H, J=5.7, 2.8 Hz), 6.97 (t, 1H, J=9.4 Hz), 6.84-6.87 (m, 1H), 4.94 (s, 2H), 3.84 (s, 2H), 3.72 (s, 3H), 3.43 (s, 2H), 2.43 (s, 3H) ppm; ¹⁹F NMR (CDCl₃) δ −128.92 ppm; ¹³C NMR (CDCl₃) δ 172.6, 159.1, 155.8 (d, J=239.1 Hz), 154.6, 147.4, 136.2, 132.1, 129.01 (2C), 127.4 (2C), 127.1 (d, J=15.3 Hz), 125.9, 116.2, 115.9 (d, J=22.9 Hz), 114.8 (d, J=7.6 Hz), 62.7, 51.80, 49.8, 46.6, 10.5; HRMS for C₂₁H₂₀ClFN₂O₄, Calcd for (M+H)⁺: 419.1174, Found: 419.1170.

d. Methyl 2-((5-((2-(4-chlorophenyl)-5-methyloxazol-4-yl)methoxy) fluorobenzyl)(methoxycarbonyl)amino)acetate

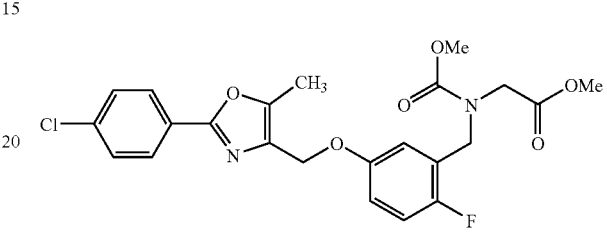

To a THF solution (15 mL) of Example 2c compound (3.9 g, 9.33 mmol) was added saturated aqueous Na₂CO₃ (10 mL) and methyl chloroformate (2.16 ml, 28 mmol). The reaction was stirred at RT for 20 min; at this time analytical HPLC indicated that the reaction was complete. The reaction was extracted with EtOAc (3×40 mL). The combined organic extracts were dried (MgSO₄) and concentrated in vacuo. The residue was chromatographed (SiO₂; 40 g ISCO column; continuous gradient from 0 to 60% EtOAc in hexanes) to afford Example 2d compound (4.2 g; 95%) as an oil ¹H NMR (CDCl₃) δ 7.91 (d, 2H, J=8.3 Hz), 7.38 (d, 2H, J=8.8 Hz), 6.98-7.0 (m, 1H), 6.94 (dd, 1H, J=14.8, 8.8 Hz), 6.85-6.90 (m, 1H), 4.90 (s, 2H), 4.55 (d, 2H, J=7.6 Hz), 3.95 (d, 2H, J=15.7 Hz), 3.73 (s, 2H, one of carbamate's methoxy group rotamer), 3.69 (s, 4H, contains another carbamate's methoxy group rotamer and the ester methoxy group), 2.40 (s, 3H) ppm; ¹⁹F NMR (CDCl₃) δ −128.31 and −128.63 ppm (rotamers); ¹³C NMR (CDCl₃) δ 169.9, 159.1, 156.9 and 156.7 (1C; rotamers), [156.6 and 154.7 (d, C—F, J=241.6 Hz), 156.4 and 154.5 (d, C—F, J=241.6 Hz)] (rotamers), 154.6, 147.4, 136.2 and 136.1 (1C; rotamers), 131.9, 128.9 (2C), 127.3 (2C), 125.8 and 125.7 (1C; rotamers), 124.8-124.5 (1C; rotamers), 115.7-116.2 (1C; rotamers), 115.4 and 115.3 (1C; rotamers), 114.8 (1C; 2 peaks; rotamers), 62.6, 53.2 and 53.1 (1C; rotamers), 52.1, 48.2 and 47.9 (1C; rotamers), 45.4 and 45.2 (1C; rotamers), 10.4; HRMS for C₂₃H₂₂ClFN₂O₆, Calcd for (M+H)⁺: 477.1229, Found: 477.1225.

Synthesis of Example 2: Glycine, N-[[3-[[2-(4-chlorophenyl)-5-methyl-4-oxazolyl]methoxy]5-fluorophenyl]methyl]-N-(methoxycarbonyl)-

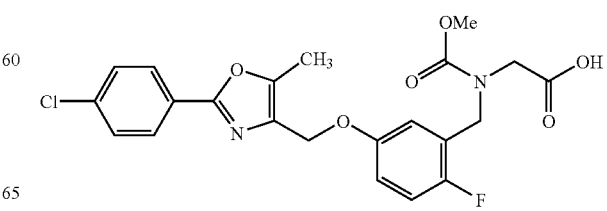

To a solution of Example 2d compound (4.2 g, 8.8 mmol) in THF (40 mL) was added aqueous NaOH (46 mL of a 1 N solution; 46 mmol). The reaction was stirred for 2 h at RT, after which HPLC indicated that the reaction was complete. The reaction was acidified with aqueous 1 N HCl to pH ~2-3 and extracted with EtOAc (3×50 mL). The combined organic extracts were dried (MgSO$_4$) and concentrated in vacuo to ~10 mL volume. MeCN (50 mL) was added, and the mixture was concentrated at 40° C. to ~30 mL volume, then was stored at 0° C. overnight. The resulting white solid was filtered off, washed with MeCN (10 mL) and dried in vacuo for 72 h to afford the title compound Example 2 (3.2 g). An additional 0.19 g of the title compound was obtained from the mother liquor by further recrystallization from MeCN. $^1$H NMR (DMSO-d$_6$) δ 7.93 (d, 2H, J=8.4 Hz), 7.58 (d, 2H, J=8.4 Hz), 7.09-7.15 (m, 1H), 6.94-6.99 (m, 1H), 6.85-6.90 (m, 1H), 4.97 and 4.96 (s, 2H, rotamers), 4.47 and 4.46 (s, 2H, rotamers), 3.91 (s, 2H), 3.60 and 3.58 (s, 3H, methoxy group rotamers), 2.43 (s, 3H) ppm; $^{19}$F NMR (DMSO-d$_6$) δ −129.04 and −129.15 ppm (rotamers); $^{13}$C NMR (DMSO-d$_6$) δ 170.8 and 170.7 (1C; rotamers), 158.0, 156.2, [155.7 and 153.8; 1C; d C—F, J=238.0 Hz), 155.6 and 153.7 (1C; d, C—F, J=236.5 Hz)] (rotamers), 154.3 (1C; 2 peaks; rotamers), 147.9, 135.0, 132.0, 129.3 (2C), 127.4 (2C), 125.6, 125.0-125.5 (1C; rotamers), 115.8-116.1 (1C; rotamers), 115.4-115.8 (1C; rotamers), 114.56-114.93 (rotamers), 61.7, 52.7, 48.8 and 47.4 (1C; rotamers), 45.6 and 45.3 (1C; rotamers), 10.0; HRMS for C$_{22}$H$_{20}$ClFN$_2$O$_6$, Calcd for (M+H)$^+$: 463.1072, Found: 463.1076; Anal. Calcd For C$_{22}$H$_{20}$ClFN$_2$O$_6$: C, 57.08; H, 4.35; Cl, 7.66; F, 4.10; N, 6.05. Found: C, 57.09; H, 4.37; Cl, 7.62; F, 4.08; N, 6.19.

Alternative Synthesis of Example 2d

Synthesis of 2e

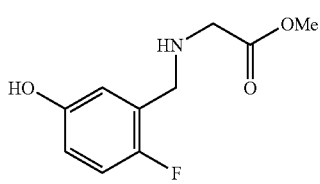

2e

To glycine methyl ester hydrochloride (0.45 g, 3.6 mmol) in dry MeOH (5 ml) was added Et$_3$N (0.5 ml, 3.6 mmol). After 5 min, Example 2a compound (0.25 g, 1.8 mmol) was added and the reaction was stirred at RT for 30 min, followed by the addition of NaBH$_4$ (0.13 g, 3.6 mmol) over 2 h in four portions. HPLC analysis showed complete reaction. MeOH (5 mL) was then added to the reaction mixture, which was then concentrated in vacuo. The residue was partitioned between EtOAc and water. The organic phase was washed with brine (10 mL), dried (MgSO$_4$), and concentrated in vacuo. The residue was chromatographed (SiO$_2$, eluting with 50% EtOAc/heptane; 2×20 mL) to afford 0.27 g of compound 2e (71% yield).

Synthesis of 2f

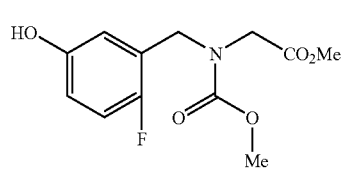

2f

To a THF (1.3 ml) solution of Example 2e compound (0.25 g, 1.2 mmol) was added saturated aqueous NaHCO$_3$ (1 mL). After cooling to 5° C., methyl chloroformate (0.09 ml, 1.2 mmol) was added with stirring. After 10 min, HPLC showed that the reaction was complete. The organic layer (pale clear yellow) was dried (Na$_2$SO$_4$), and concentrated in vacuo to give crude 2f compound as a pale yellow oil (0.40 g), which was used in the next reaction without further purification.

Alternate Synthesis of 2d

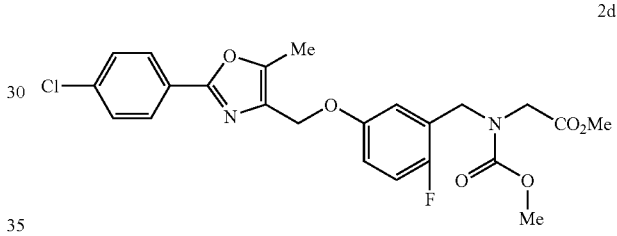

2d

A cloudy white slurry of crude Example 2f compound (0.32 g, ≦1.2 mmol), Example 1a compound (0.29 g, 1.2 mmol), and K$_2$CO$_3$ (0.5 g, 3.6 mmol) in MeCN (5 mL) was heated at 55° C. for 4 h. At this point, HPLC showed <2% of unreacted compound 2f remained. The reaction was cooled to RT and saturated aqueous NH$_4$Cl (5 mL) was added; the aqueous layer was extracted with EtOAc (2×10 mL). The combined organic extracts were dried (Na$_2$SO$_4$) and concentrated in vacuo. The crude product was purified by silica gel chromatography as previously described for 2d to give 0.44 g of Example 2d compound as a clear oil. The $^1$H-NMR spectrum is consistent with the sample of Example 2d compound prepared using the previous synthetic route.

Biological Data

In vitro PPAR agonist functional assays were performed by transiently transfecting GAL4-hPPARα-LBD or GAL4-hPPARγ-LBD constructs respectively into HEK293 (human embryonic kidney) cells stably expressing 5×GAL4RE-Luciferase. Agonist binding results in an increase in luciferase enzyme activity which can be monitored by measuring luminescence upon cell lysing and the addition of luciferin substrate. EC$_{50}$ values (µM) for PPARα or γ agonist activity were calculated as the concentration of the test ligand (µM) required for the half-maximal activity in HEK293 cells. The efficacy of a test ligand is defined as its maximum activity as compared to the maximal activity of the primary standards, 100 µM fenofibric acid for PPARα and 1 µM rosiglitazone for PPARγ, reported as % efficacy. Compounds of formula I are functional agonists with activities in the range of $EC_{50}$=1-10 nM against the human PPARα receptor and $EC_{50}$>4000 nM against the human PPARγ receptor. The ratios of the PPARγ: PPARα $EC_{50}$ values of compounds of formula I are between 400 and 1100 in this functional assay.

TABLE 1

In vitro functional data for Compounds 1-2

| Compound | PPARα $EC_{50}$ (nM) (% efficacy) | PPARγ $EC_{50}$ (nM) (% efficacy) |
|---|---|---|
| 1 | 10 ± 3 (81 ± 14%) | 4090 ± 1741 (83 ± 8%) |
| 2 | 4 ± 1 (81 ± 10%) | 4511 ± 1314 (67 ± 13%) |

The present PPARα selective agonists/activators of Formula I are more potent in a GAL4 functional transactivation assay in a HEK (human embryonic kidney) cell line than the current marketed PPARα selective agonists (fibrates). The current fibrates are weak PPARα ligands, and have modest efficacy in modulating serum lipids.

It is known by one skilled in the art that the compounds of the present invention decrease plasma triglycerides and cholesterol levels at doses ≧10 mg/kg in rodent models of atherosclerosis and dyslipidemia (e.g. the high fat-fed hamster model). The typical administration of said compounds is expected to be between 0.1 to 2,000 mg/day in the clinical setting, and is preferably between 0.5 to 100 mg/day. (Reference for high fat-fed hamster model as an in vivo rodent model for anti-atherosclerosis efficacy: P-R Wang et al., *Eur. Journ. of Pharm.*, 2001, 427, 285-293).

Male Golden Syrian Hamster (*Mesocricetus auratus*), 7-10 weeks of age and weighing 110-120 grams, were put on a high fat diet (D11953) for two weeks. The high fat diet was formulated by Research Diets, Inc, New Brunswick, N.J. using Purina 5001 as the base diet. Final composition (% by weight) of the diet is: 11.5% coconut oil, 11.5% corn oil, 0.5% cholesterol and 5% fructose. Hamsters were then dosed orally once daily with the Example 1 or 2 compounds using a vehicle comprised of 5% Cremaphore, 5% ethanol, 10% 1-methyl-pyrrolidinone, and 80% water. Plasma samples were obtained from hamsters fasted overnight (18 hours after last administration of compound) on day 22. The plasma triglyceride and cholesterol levels were determined and the percentage reductions in both parameters of drug-treated animals relative to vehicle-treated animals are shown in Table 2 below.

TABLE 2

| Compound (10 mg/kg orally dosed once daily for 14 days) | % Reduction in Plasma Total Cholesterol vs Vehicle-control group | % Reduction in Plasma Triglycerides vs Vehicle-control group |
|---|---|---|
| 1 | −38% | −77% |
| 2 | −60% | −85% |

What is claimed is:

1. A compound having the structure of Formula (Ia):

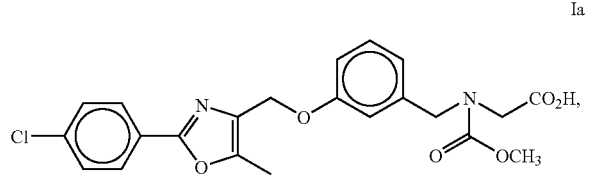

Ia and salts thereof.

2. A compound having the structure of Formula (Ib):

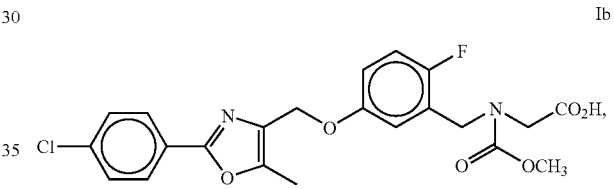

Ib and salts thereof.

3. A pharmaceutical composition comprising a compound as defined in claim 1 and a pharmaceutically acceptable carrier thereof.

4. A pharmaceutical composition comprising a compound as defined in claim 2 and a pharmaceutically acceptable carrier therefor.

* * * * *